United States Patent
Tsutsumida et al.

(10) Patent No.: US 8,083,995 B2
(45) Date of Patent: Dec. 27, 2011

(54) SAMPLE PROCESSING APPARATUS AND SAMPLE PROCESSING SYSTEM

(75) Inventors: Keisuke Tsutsumida, Kobe (JP); Ryuichiro Ebi, Osaka (JP); Rumi Takata, Kobe (JP); Akio Toyoda, Kobe (JP)

(73) Assignee: Sysmex Corporation, Hyogo (JP)

( * ) Notice: Subject to any disclaimer, the term of this patent is extended or adjusted under 35 U.S.C. 154(b) by 313 days.

(21) Appl. No.: 12/035,238

(22) Filed: Feb. 21, 2008

(65) Prior Publication Data
US 2008/0206098 A1 Aug. 28, 2008

(30) Foreign Application Priority Data
Feb. 22, 2007 (JP) ................................. 2007-042263

(51) Int. Cl.
*G01N 21/00* (2006.01)
*G01N 31/00* (2006.01)
*G01N 33/00* (2006.01)
*G01N 35/00* (2006.01)

(52) U.S. Cl. ................. 422/65; 422/63; 436/43; 436/47
(58) Field of Classification Search .................... 422/65; 436/47
See application file for complete search history.

(56) References Cited

U.S. PATENT DOCUMENTS

| | | | |
|---|---|---|---|
| 6,019,945 A * | 2/2000 | Ohishi et al. ..................... | 422/65 |
| 6,331,437 B1 * | 12/2001 | Cohen et al. ..................... | 436/43 |
| 6,764,650 B2 * | 7/2004 | Takahashi et al. .............. | 422/65 |
| 7,331,474 B2 * | 2/2008 | Veiner et al. ................... | 422/104 |
| 2004/0134750 A1 * | 7/2004 | Luoma, II ..................... | 198/340 |
| 2005/0036912 A1 * | 2/2005 | Yamakawa et al. ............. | 422/65 |
| 2005/0186113 A1 * | 8/2005 | Koike et al. ..................... | 422/63 |
| 2006/0216199 A1 | 9/2006 | Koike | |

FOREIGN PATENT DOCUMENTS

JP 08-015271 A 1/1996

* cited by examiner

*Primary Examiner* — Jill Warden
*Assistant Examiner* — Charles D Hammond
(74) *Attorney, Agent, or Firm* — Sughrue Mion, PLLC

(57) ABSTRACT

The present invention is to present a sample processing system that is capable of reducing the tasks involved in the connection of the transporting apparatus. The sample processing system comprises: the transporting apparatus 11 for transporting the sample container 32 to a predetermined position; and the analyzer 10 for analyzing the sample contained in the sample container 32 transported to the predetermined position, the analyzer 10 comprising: the connection part 15 for connecting the transporting apparatus 11; the aspirating part 10a for aspirating the sample contained in the sample container 32; the apparatus body 12 for measuring the sample aspirated by the aspirating part 10a; the input part 29 for inputting identification information for identifying a type of the transporting apparatus 11; and the control unit 16 for controlling an operation of the transporting apparatus 11 based on the identification information input by the input part 29.

17 Claims, 25 Drawing Sheets

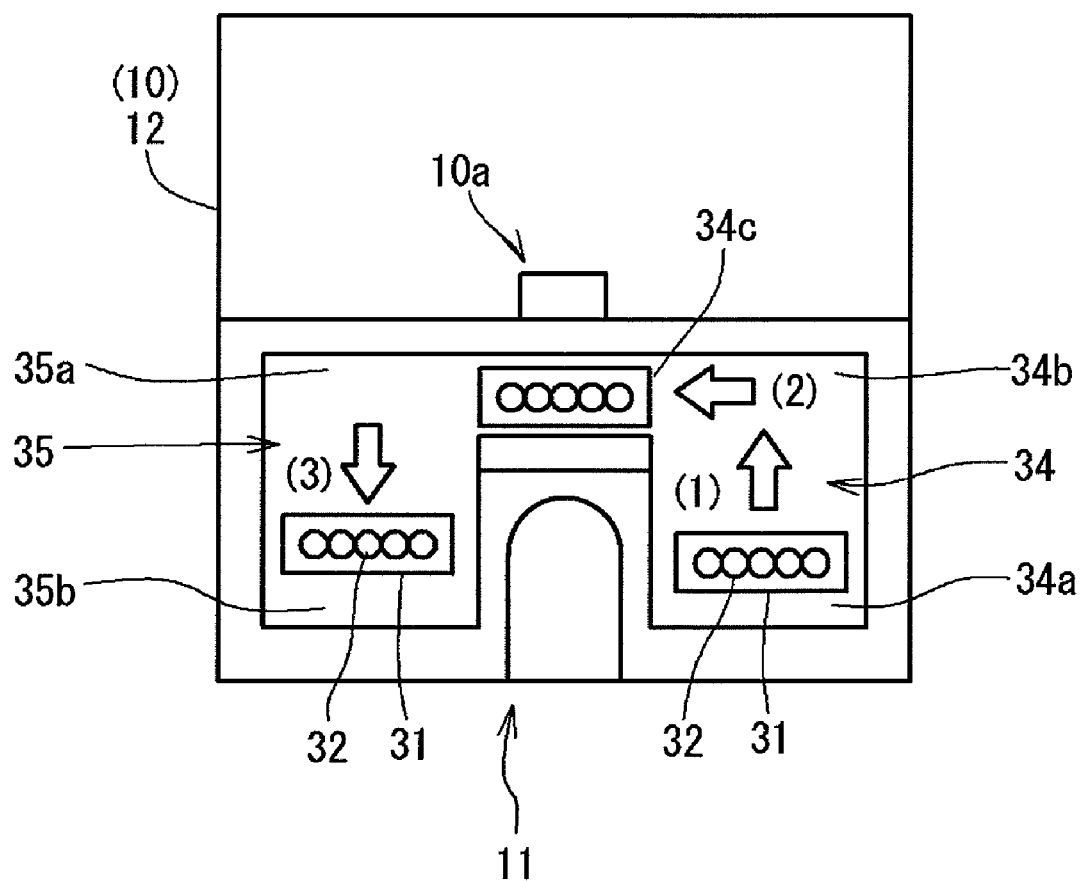

Fig. 18

| | Set value | Content |
|---|---|---|
| Standard mode | 0 | Mode not connected with transporting apparatus Only manual measurement can be performed |
| Transporting apparatus X mode | 1 | Mode for using transporting apparatus X Transporting apparatus measurement can be performed with ten-specimen rack |
| Transporting apparatus Y mode | 2 | Mode for connecting transporting apparatus Y |
| Transporting apparatus Z mode | 3 | Mode for connecting transporting apparatus Z |
| Transporting apparatus W mode | 4 | M Mode for using transporting apparatus W Transporting apparatus measurement can be performed with five-specimen rack |

Fig. 19
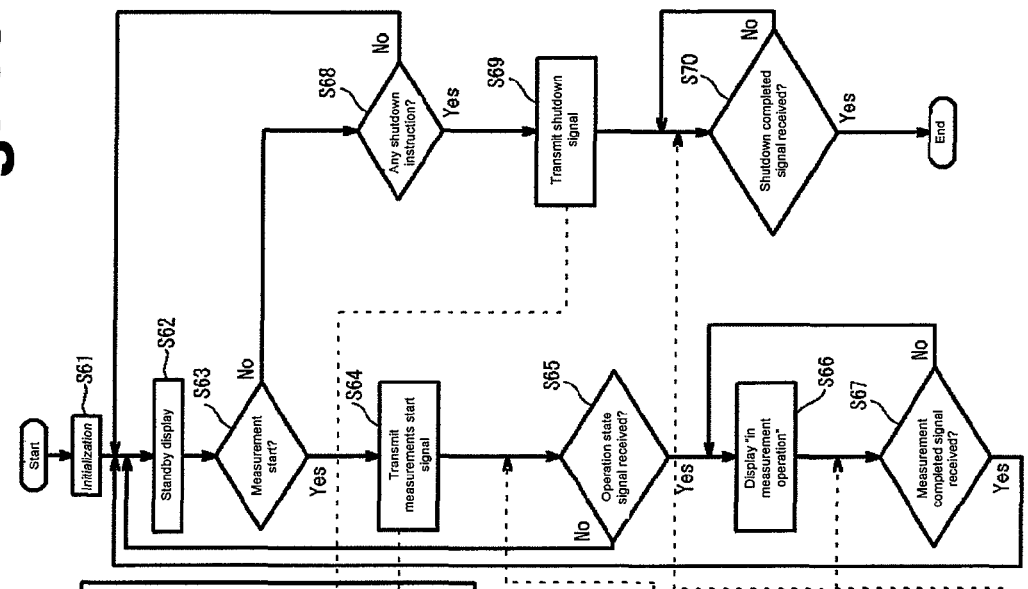
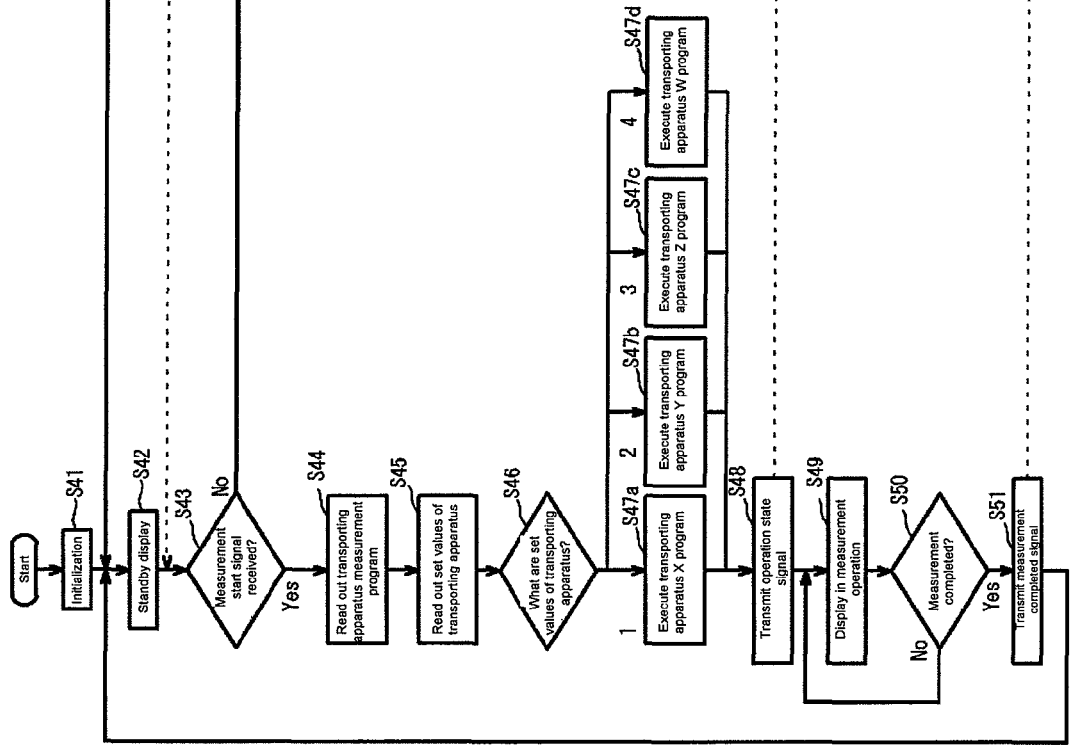

Fig. 22

| Pattern | First detection sensor state | First detection sensor output | Second detection sensor state | Second detection sensor output | Type of transporting apparatus |
|---|---|---|---|---|---|
| 1 | Light shield | Low level | Light shield | Low level | Transporting apparatus X |
| 2 | Light shield | Low level | Light incident | High level | Transporting apparatus Y |
| 3 | Light incident | High level | Light shield | Low level | Transporting apparatus Z |
| 4 | Light incident | High level | Light incident | High level | No transporting apparatus |

SAMPLE PROCESSING APPARATUS AND SAMPLE PROCESSING SYSTEM

FIELD OF THE INVENTION

The present invention relates to a sample processing apparatus and a sample processing system for performing examination, measurement, analysis, and the like on a sample such as blood and urine.

BACKGROUND

Japanese Laid-Open Patent Publication No. 8-15271 discloses a rack transporting apparatus, connected to an examination apparatus examining a sample such as blood and urine, for automatically supplying the sample to the examining apparatus. The rack transporting apparatus transports the rack holding a plurality of sample containers in the front and back direction and in the left and right direction, and sequentially arranges each sample container at an aspirating position facing a sample aspirating part of the examination apparatus. The examination apparatus normally operates in conjunction with the rack transporting apparatus to aspirate the sample from the sample container arranged at the aspirating position facing the sample aspirating part and to perform the examination according to a predetermined procedure.

The type of rack transporting apparatus connected to the examination apparatus differs depending on the facility where the examination apparatus is installed, and so on. Different rack transporting apparatuses may be connected to one type of examination apparatus depending on the facilities. If the rack transporting apparatus connected to the examination apparatus differs, the configuration, the operation, and the operation control of a transport driving unit thereof differ. Thus, the program for controlling the operation of the rack transporting apparatus differs. In this case, the task of incorporating the program corresponding to the type of rack transporting apparatus in the examination apparatus, various setting tasks and checking tasks are normally required every time for each facility installed with the rack transporting apparatus. Thus, great amount of trouble and time are required. Similar tasks are required when replacing the already installed rack transporting apparatus with a different type, and thus the efficiency is very bad.

SUMMARY

A first aspect of the present invention is a sample processing system for processing a sample contained in a sample container, comprising: a transporting apparatus for transporting a sample container to a predetermined position; and a sample processing apparatus for processing a sample contained in the sample container transported to the predetermined position by the transporting apparatus, the sample processing apparatus comprising: a connection part for connecting the transporting apparatus with the sample processing apparatus; an aspirating part for aspirating the sample contained in the sample container transported to the predetermined position by the connected transporting apparatus; a processing part for performing a predetermined process to the sample aspirated by the aspirating part; identification information obtaining means for obtaining identification information for identifying a type of the connected transporting apparatus; and transport controlling means for controlling an operation of the connected transporting apparatus based on the identification information obtained by the identification information obtaining means.

A second aspect of the present invention is a sample processing system for processing a sample contained in a sample container, the sample processing system comprising: a transporting apparatus for transporting a sample container to a predetermined position; and a sample processing apparatus for processing a sample contained in the sample container transported to the predetermined position by the transporting apparatus, wherein the sample processing apparatus comprises: a connection part for connecting the transporting apparatus with the sample processing apparatus; an aspirating part for aspirating the sample contained in the sample container transported to the predetermined position by the connected transporting apparatus; a processing part for performing a predetermined process on the sample aspirated by the aspirating part; identification information obtaining means for obtaining identification information for identifying a type of the connected transporting apparatus; and a first communication part for transmitting an operation instructing command to the transporting apparatus based on the identification information obtained by the identification information obtaining means; and wherein the transporting apparatus further comprises: a second communication part for receiving the operation instructing command transmitted from the first communication part; and transport controlling means for controlling an operation of the transporting apparatus based on the operation instructing command received by the second communication part.

A third aspect of the present invention is a sample processing apparatus for processing a sample contained in a sample container, the sample processing apparatus comprising: a connection part for connecting a transporting apparatus with the sample processing apparatus, the transporting apparatus transporting a sample container to a predetermined position; an aspirating part for aspirating a sample contained in the sample container transported to the predetermined position by the connected transporting apparatus; a processing part for performing a predetermined process on the sample aspirated by the aspirating part; identification information obtaining means for obtaining identification information for identifying a type of the connected transporting apparatus; and a controller for executing a control process for operating the connected transporting apparatus based on the identification information obtained by the identification information obtaining means.

BRIEF DESCRIPTION OF THE DRAWINGS

FIG. 7 is a schematic plan view of the analyzer and the transporting apparatus according to the first embodiment of the present invention;

FIG. 18 is a table showing a relationship between the type and the set value of the transporting apparatus;

FIG. 19 is a flowchart showing a procedure for the analyzer to perform a transporting apparatus measurement mode according to the first embodiment of the present invention;

FIG. 22 is a table showing a relationship between the state and the output of the detection means, and the transporting apparatus;

DETAILED DESCRIPTION OF THE EMBODIMENT

First Embodiment

An analyzer 10 for analyzing particles in urine according to a first embodiment of the present invention will be described.
[Configuration of Analyzer 10 for Analyzing Particles in Urine]

Figure 1:
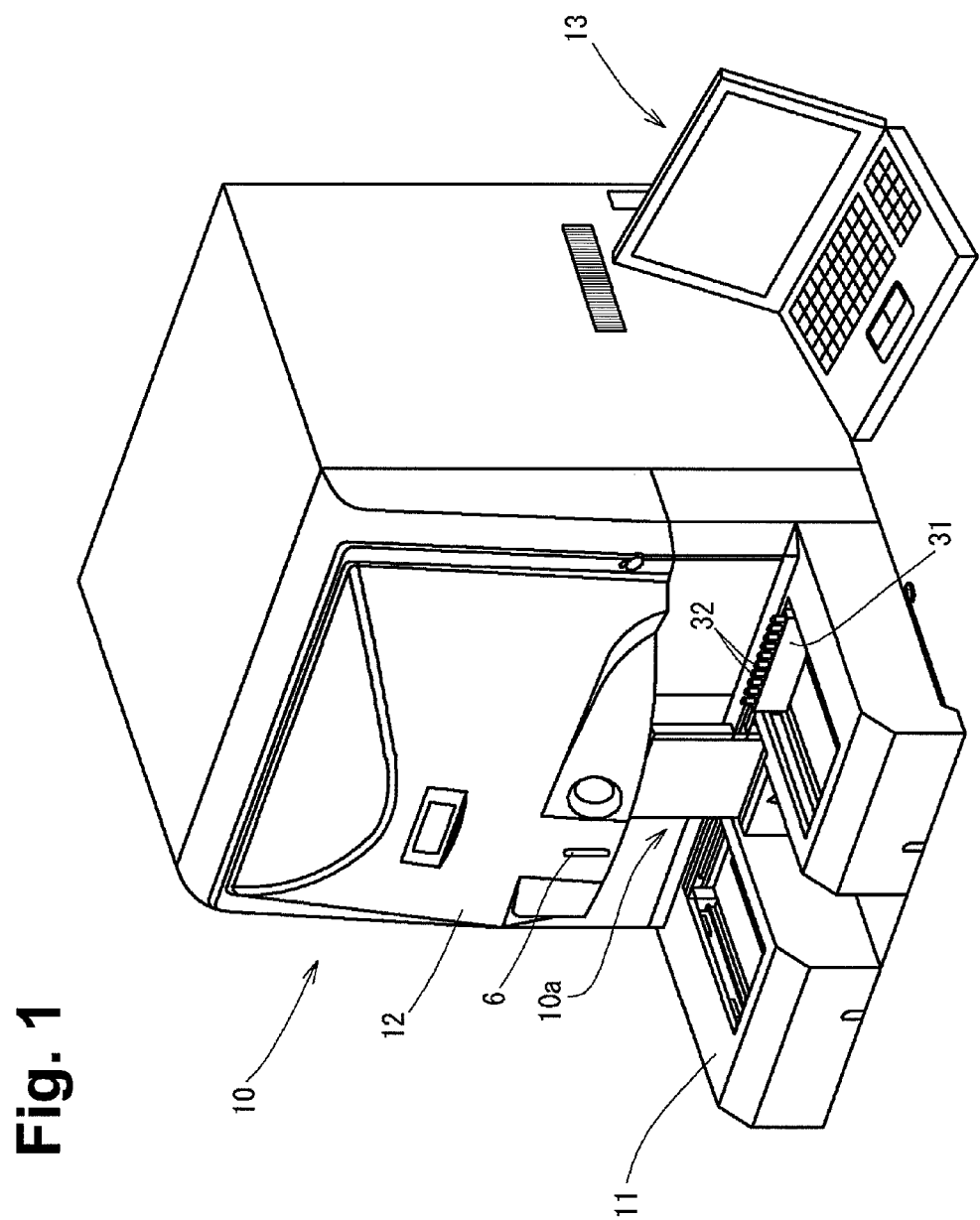
FIG. 1 is a perspective view showing a state in which a transporting apparatus is connected to an analyzer (sample processing apparatus) according to a first embodiment of the present invention.

The analyzer for analyzing particles in urine (hereinafter simply referred to as analyzer) 10 aspirates the sample transported by a transporting apparatus 11 and detects information of particles such as red blood cells and bacteria from the sample. As shown in FIG. 1, the analyzer 10 includes an apparatus body 12 for performing measurement etc. of the sample, and a system controller 13, connected to the apparatus body 12, for performing analysis etc. of the measurement result.

Figure 2:
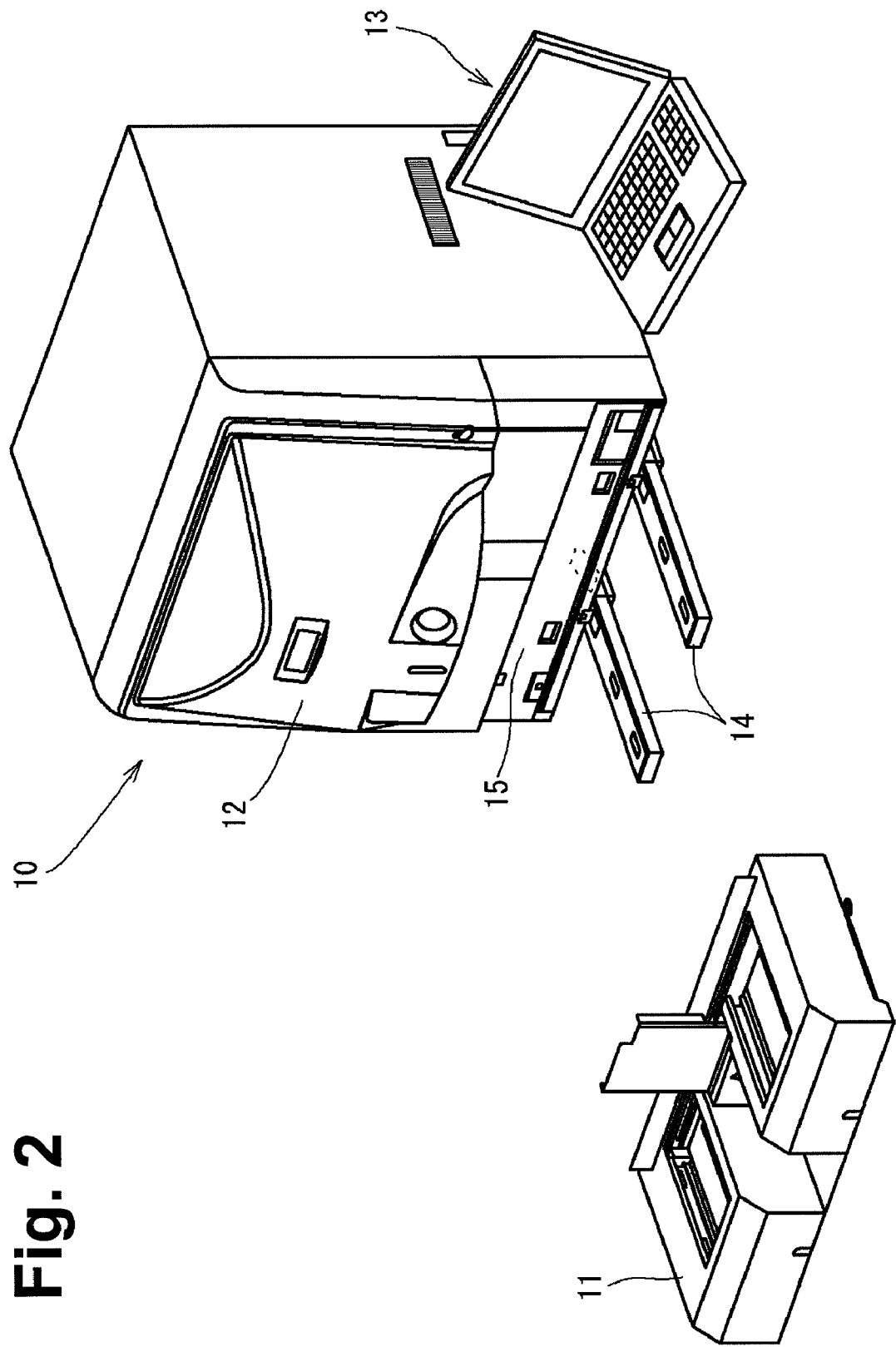
FIG. 2 is a perspective view showing a state in which the transporting apparatus is disconnected from the analyzer according to the first embodiment of the present invention.

As shown in FIG. 2, a transporting apparatus connection part 15 to which the transporting apparatus 11 is detachably connected is arranged at the lower part of the front surface of the apparatus body 12. Two supporting legs 14 are arranged at the bottom surface of the apparatus body 12, where each supporting leg 14 is projected towards the front side from the front surface of the apparatus body 12. The transporting apparatus 11 connected to the apparatus body 12 is mounted on the supporting legs 14 and supported by the supporting legs 14. A plurality of types of transporting apparatuses can be connected to the transporting apparatus connection part 15 as hereinafter described.

Figure 3:
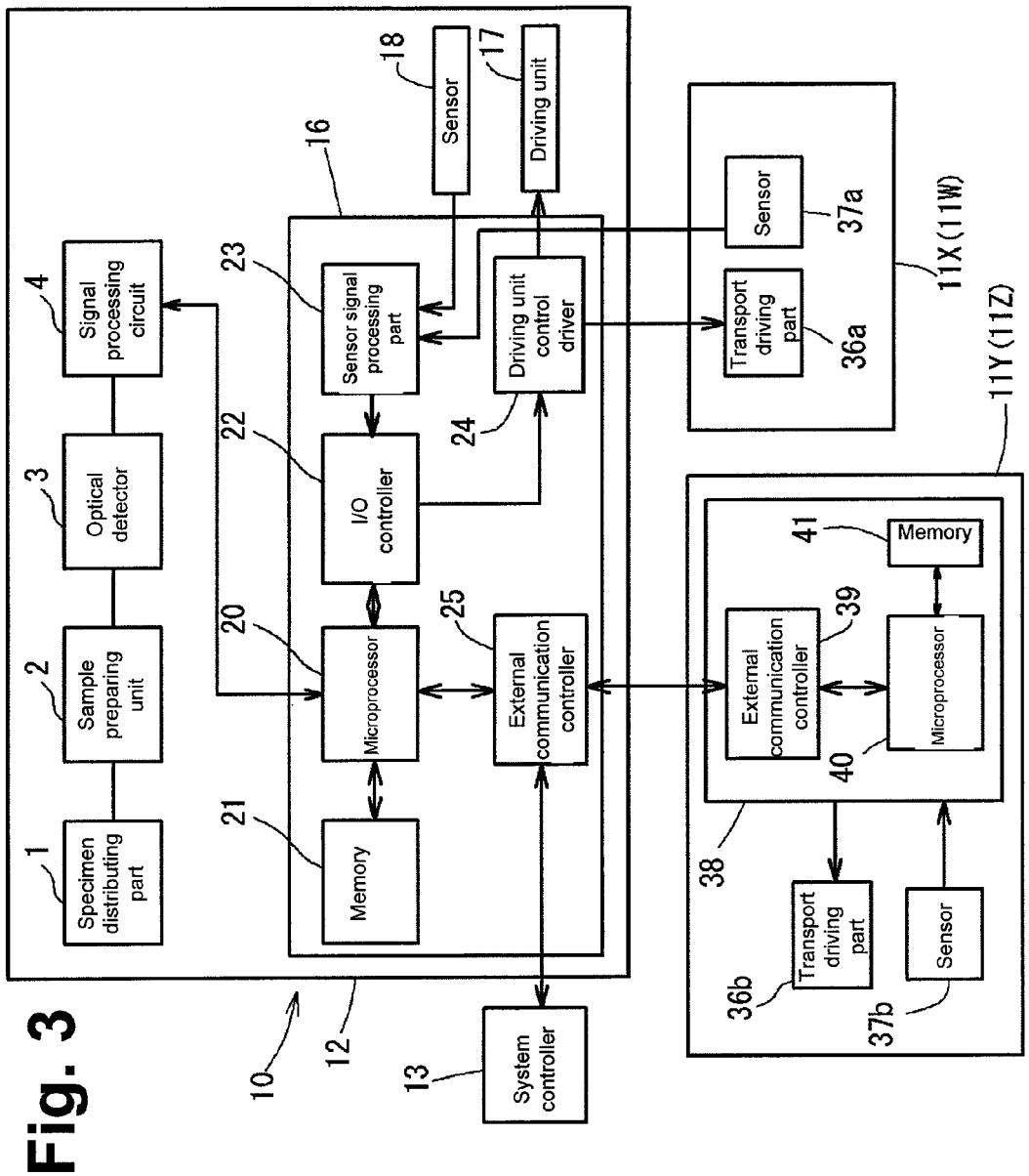
FIG. 3 is a block diagram of the analyzer and the transporting apparatus according to the first embodiment of the present invention.

As shown in FIG. 3, the apparatus body 12 of the analyzer 10 includes a sample distributing part 1 for dispensing urine (sample) in a test tube (not shown), a sample preparing unit 2 for preparing a measurement sample from the sample dispensed from the sample distributing part 1, an optical detector 3 for detecting information on the particles such as red blood cells and the bacteria from the measurement sample, a signal processing circuit 4, a measurement control unit 16, a driving unit 17 such as motor, actuator and valve, and various sensors 18. The measurement control unit 16 controls the aspiration of the urine and the measurement by controlling the operation of the driving unit 17 while processing the signal of the sensor 18. In FIG. 3, two types of transporting apparatuses 11X (11W) and 11Y (11Z) are shown, but actually, either one type is connected to the analyzer 10.
[Configuration of Measurement Control Unit 16]

The measurement control unit 16 includes a microprocessor 20, a memory 21, an I/O controller 22, a sensor signal processing part 23, a driving unit control driver 24, and an external communication controller 25. The memory 21 includes a ROM, a RAM, and the like, and the ROM stores a control program for controlling the driving unit 17 and data necessary for the execution of the control program. The microcomputer 20 loads the control program in the RAM or can directly execute the program from the ROM.

The signal of the sensor 18 is transmitted to the microprocessor 20 via the sensor signal processing part 23 and the I/O controller 22. The microprocessor 20 executes the control program and controls the driving unit 17 through the I/O controller 22 and the driving unit control driver 24 in response to the signal.

The data processed by the microprocessor 20 and the data necessary for the processing of the microprocessor 20 are transmitted and received with an external apparatus such as the system controller 13 by way of the external communication controller 25. As hereinafter described, a program for various transporting apparatuses 11 is also incorporated in the memory 21 of the measurement control unit 16.
[Configuration of System Controller 13]

Figure 4:
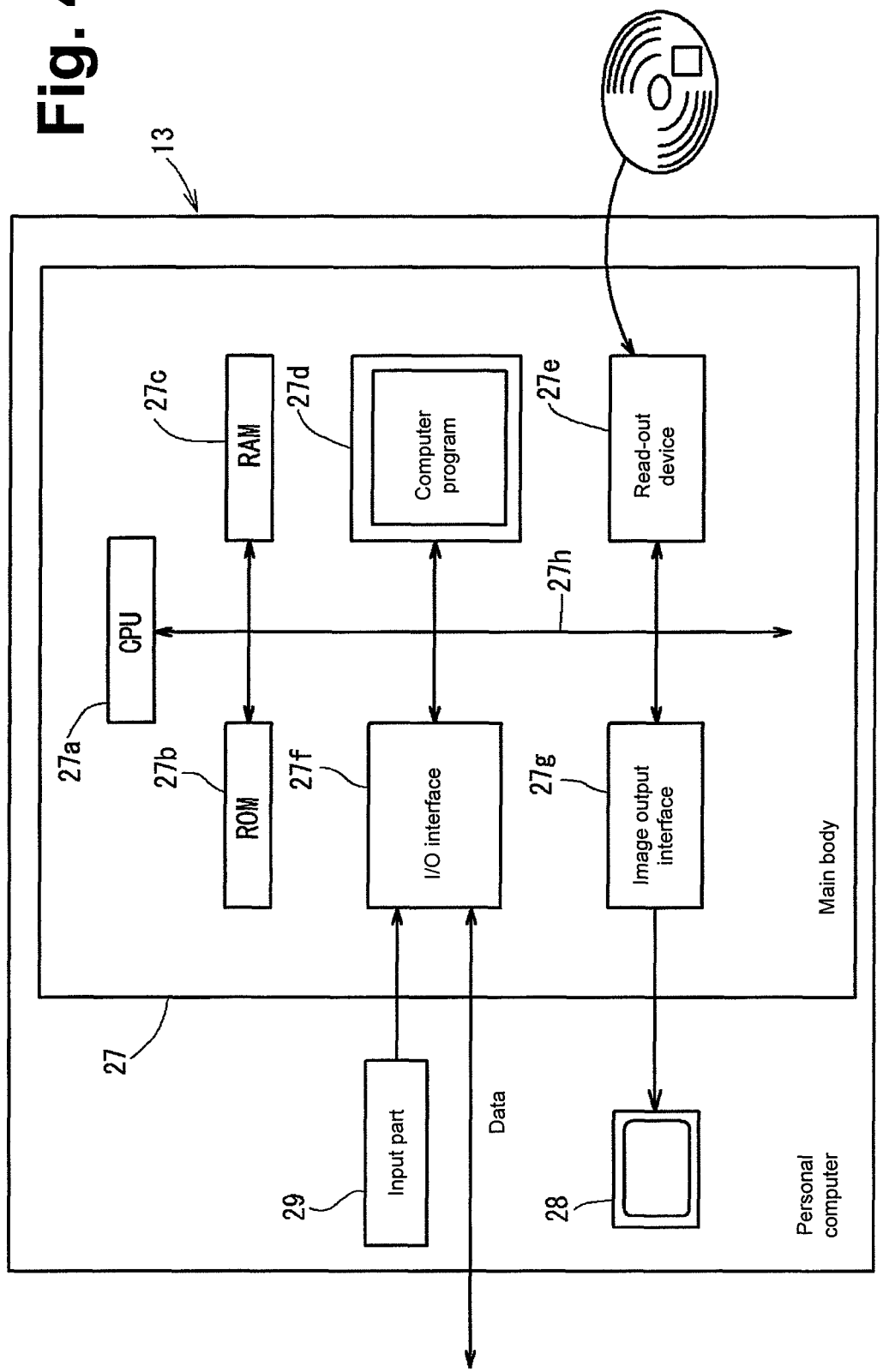
FIG. 4 is a block diagram of a personal computer configuring a system controller.

As shown in FIG. 4, the system controller 13 includes a personal computer etc., and is mainly configured by a main body 27, a display 28, and an input part 29. The main body 27 is mainly configured by a CPU 27a, a ROM 27b, a RAM 27c, a hard disc 27d, a read-out device 27e, an input/output interface 27f, and an image output interface 27g. Such components are communicably connected by a bus 27h.

The CPU 27a executes computer programs stored in the ROM 27b and the computer programs loaded in the RAM 27c. The ROM 27b is configured by mask ROM, PROM, EPROM, EEPROM, and the like, and is recorded with computer programs to be executed by the CPU 27a, data used for the same, and the like. The RAM 27c is configured by SRAM, DRAM, and the like. The RAM 27c is used to read out the computer programs recorded on the ROM 27b and the hard disc 27d. The RAM 27c is used as a work region of the CPU 27a when executing the computer programs.

The hard disc 27d is installed with various computer programs to be executed by the CPU 27a such as operating system and application program, as well as data used in executing the computer program. For instance, operating system providing graphical user interface environment such as Windows (registered trademark) manufactured and sold by US Microsoft Co. is installed in the hard disc 27d.

An operation program for performing transmission of a measurement order (operation command) to the measurement control unit 16 of the analyzer 10, reception and processing of the measurement result measured in the apparatus body 12, display of the processed analysis result, and the like is installed in the hard disc 27d. The operation program operates on the operating system.

The read-out device 27e is configured by flexible disc drive, CD-ROM drive, DVD-ROM drive, and the like, and is able to read out computer programs and data recorded on a portable recording medium. The input/output interface 27f is configured by serial interface such as USB, IEEE1394, RS-232C; parallel interface such as SCSI, IDE, IEEE1284; analog interface such as D/A converter, A/D converter, and the like. The input part 29 such as keyboard and mouse is connected to the input/output interface 27f, so that the user can input data to the personal computer using the input part 29. The input/output interface 27f is connected to the apparatus body 12, so that data etc. can be transmitted and received with respect to the apparatus body 12.

The image output interface 27g is connected to the display 28 configured by LCD, CRT, or the like, and is configured to output an image signal corresponding to the image data provided from the CPU 27a to the display 28. The display 28 displays the image (screen) according to the input image signal.

[Configuration of Sample Distributing Part 1, Sample Preparing Unit 2, and Optical Detector 3]

Figure 5:
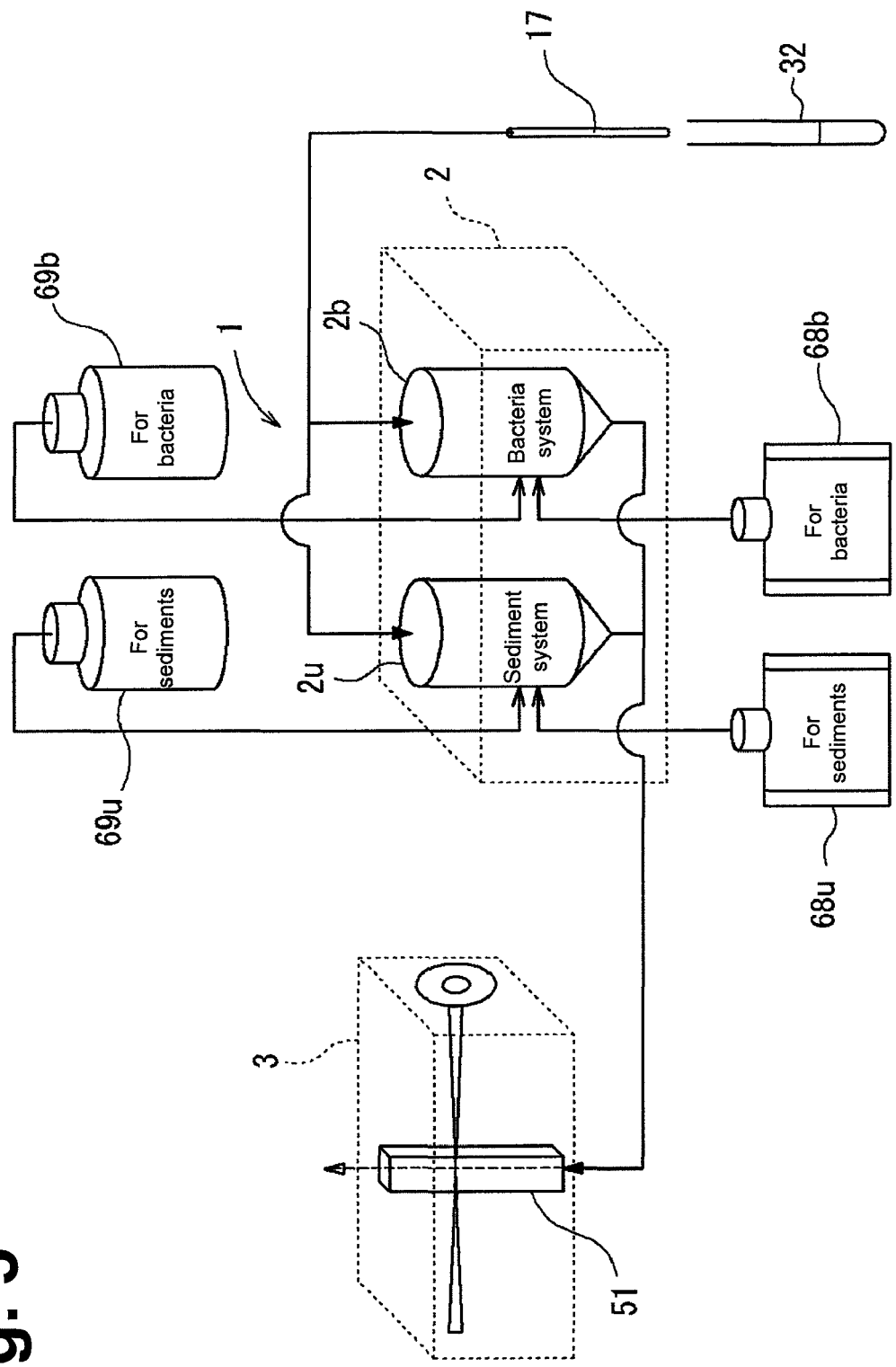
FIG. 5 is a view showing a schematic functional configuration of a sample distributing part, a sample preparing unit, and an optical detector.

As shown in FIG. 5, the urine (sample) in the test tube 32 is aspirated by a syringe pump (not shown) using an aspirate tube 17, and dispensed into the sample preparing unit 2 by the sample distributing part 1. The sample preparing unit according to the present embodiment is configured by a sample preparing part (first sample preparing part) 2u and a sample preparing part (second sample preparing part) 2b, and the sample distributing part 1 distributes the quantitated aliquot of the urine (sample) to each of the sample preparing part 2u and the sample preparing part 2b.

The urine aliquot of the sample preparing part 2u is mixed with a diluted solution 69u and a stain solution (stain reagent) 68u. The urine aliquot of the sample preparing part 2u is then stained by the pigment contained in the stain solution (stain reagent) 68u, so that the urine aliquot becomes a suspension for analyzing a relatively large particles such as red blood cells, white blood cells, epidermal cells, casts, and the like. The urine aliquot of the sample preparing part 2b, on the other hand, is mixed with a diluted solution 69b and a stain solution (stain reagent) 68b. The urine aliquot of the sample preparing part 2b is then stained by the pigment contained in the stain solution (stain reagent) 68b, so that the urine aliquot becomes a suspension for analyzing bacteria.

Of the two types of suspensions (measurement samples) prepared as above, the suspension (first measurement sample) of the sample preparing part 2u is first guided to the optical detector 3 forming a thin flow enveloped by sheath solution in a sheath flow cell 51, and irradiated with laser light. There- after, the suspension (second measurement sample) of the sample preparing part 2b is similarly guided to the optical detector 3 forming a thin flow in the sheath flow cell 51, and irradiated with laser light. Such operations are automatically performed by operating the driving unit 17 etc. by the control of the measurement control unit 16 as hereinafter described.

Figure 6:
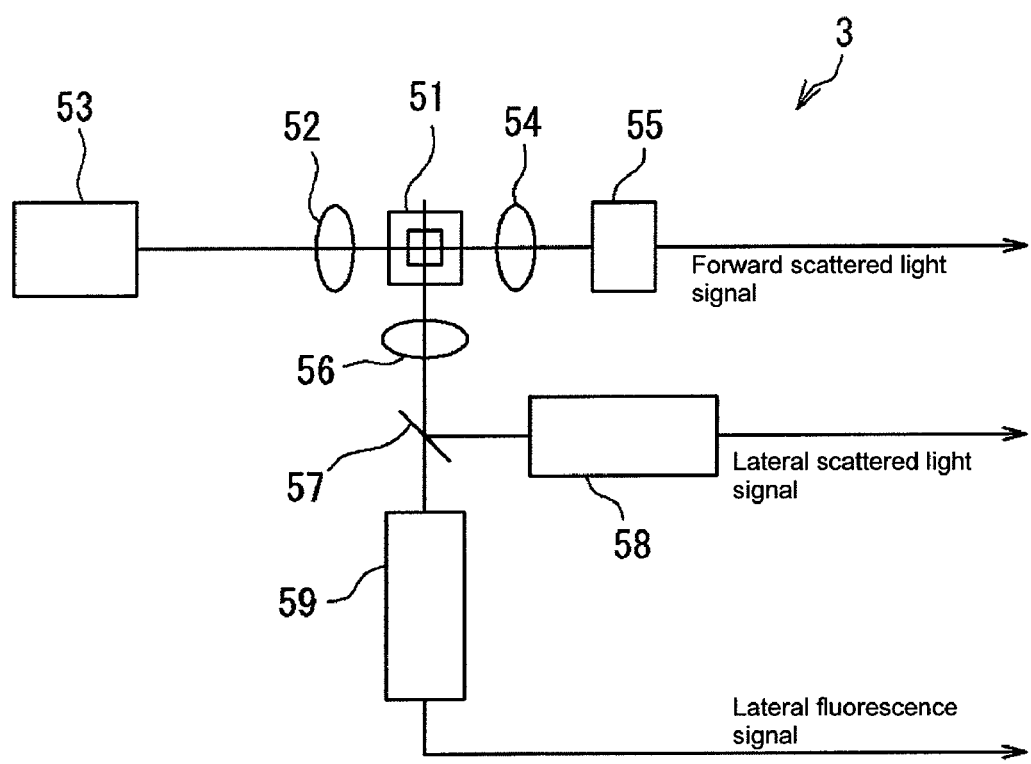
FIG. 6 is a view showing a configuration of the optical detector.

FIG. 6 is a view showing a configuration of the optical detector 3. In the figure, a condenser lens 52 collects the laser light emitted from a semiconductor laser 53 serving as a light source on the sheath flow cell 51, and a light collecting lens 54 collects a forward scattered light of the particles in the urine on a photodiode 55 serving as a scattered light receiving part. Another light collecting lens 56 collects a lateral scattered light and a lateral fluorescence of the particles on a dichroic mirror 57. The dichroic mirror 57 reflects the lateral scattered light towards a photomultiplier 58 serving as a scattered light receiving part, and transmits the lateral fluorescence towards a photomultiplier 59 serving as a fluorescence receiving part. The optical signals reflect the characteristics of the particles in the urine. The photodiode 55, the photomultiplier 58, and the photomultiplier 59 convert the light signal to an electrical signal and respectively output a forward scattered light signal (FSC), a lateral scattered light signal (SSC), and a lateral fluorescence signal (SFL). The output is amplified by a preamplifier (not shown) and provided to the signal processing circuit 4 (FIG. 3).

The forward scattered light signal (FSC), the lateral scattered light signal (SSC), and the lateral fluorescence signal (SFL) processed in the signal processing circuit 4 are sent to the system controller 13 via the external communication controller 25 by the microprocessor 20. In the system controller 13, a scattergram for analyzing the particles in the urine is formed based on the forward scattered light signal (FSC), the lateral scattered light signal (SSC), and the lateral fluorescence signal (SFL), and using this scattergram, the particles in the sample is classified into red blood cells, white blood cells, epidermal cells, casts, bacteria and the like.

As for the light source, a gas laser may be used in place of the semiconductor laser, but the semiconductor laser is preferably used in terms of low cost, compactness, and low power consumption, so that the manufacturing cost can be reduced and miniaturization as well as power saving of the apparatus can be achieved through the use of the semiconductor laser. Among the semiconductor lasers, a red semiconductor laser is preferably used as it is low cost, has long lifespan, and supply from the manufacturing company is stable.

[Configuration of Transporting Apparatus 11]

As shown in FIG. 1, the transporting apparatus 11 is connected to the front part of the apparatus body 12 of the analyzer 10. The transporting apparatus 11 has a function of transporting a plurality of test tubes (sample containers) 32 held in the rack 31 to the aspirating position facing the sample aspirating part 10a of the analyzer 10 to supply the sample to the analyzer 10. The rack 31 is held with the plurality of test tubes 32 lined in one row.

As shown in FIG. 7, a rack set region 34 for setting the rack 31 holding the test tube 32 in which a non-processed sample is accommodated is arranged on the right side of the transporting apparatus 11, and a rack accommodating region 35 for accommodating the rack 31 holding the test tube 32 in which the processed sample is accommodated is arranged on the left side of the transporting apparatus 11. A transport path 34c is formed between a terminating position 34b of the rack set region 34 and a starting position 35a of the rack accommodating region.

The plurality of racks 31 having the longitudinal direction directed in the left and right direction can be arranged in the front and back direction in the rack set region 34 and the rack accommodating region 35. In the rack set region 34, each rack 31 is transported from the starting position 34a on the near side towards the terminating position 34b on the back side as shown with an arrow (1), and thereafter, transported towards the left (direction of arrow (2)) on the transport path 34c towards the starting position 35a of the rack accommodating region 35. The central part of the transport path 34c is the aspirating position of the sample aspirating part 10a. The aspirating position is a position facing the sample aspirating part 10a. Each test tube 32 is sequentially arranged facing the sample aspirating part 10a of the analyzer 10 while transporting the rack 31 towards the left on the transport path 34c. The sample is aspirated from the test tube 32 of the rack 31 arranged at the aspirating position by the sample aspirating part 10a. After aspiration is terminated, the test tube 32 adjacent to the test tube 32, which sample has been aspirated, is then arranged at the aspirating position, and the sample of the test tube 32 arranged at the aspirating position is aspirated. The rack 31 is transported to the starting position 35a of the rack accommodating region 35 when the aspiration of the sample from all the test tubes 32 accommodated in the rack 31 is terminated by repeating such operation. The rack 31 transported to the starting position 35a is transported towards the terminating position 35b on the near side as shown with an arrow (3). In this manner, all the racks 31 set in the rack set region 34 are accommodated in the rack accommodating region 35 when aspiration of the sample from all the test tubes 32 accommodated in the rack 31 is terminated.

[Type of Transporting Apparatus 11]

Figure 8A:
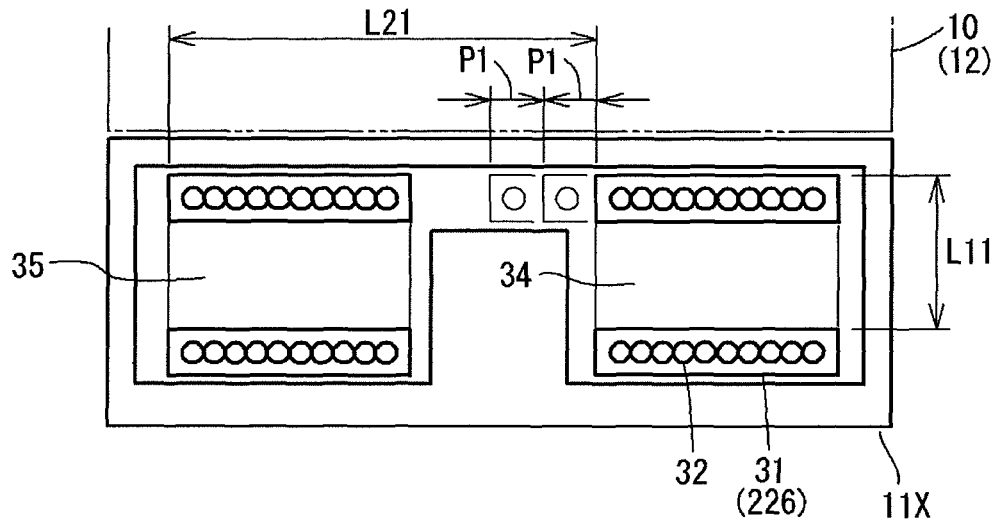
FIG. 8(a) is a plan view showing a transporting apparatus X.
Figure 8B:
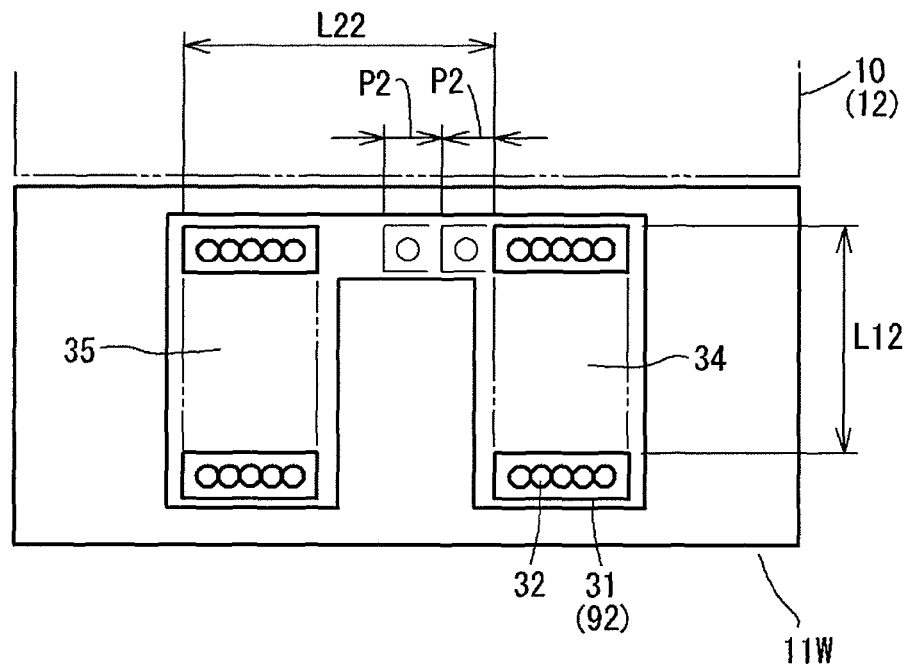
FIG. 8(b) is a plan view showing a transporting apparatus W.

The transporting apparatus 11 has a plurality of types depending on the size etc. of the rack 31 to be transported. FIGS. 8(a) and 8(b) show transporting apparatuses 11X and 11W for transporting two types of racks 31 in which the number of test tubes 32 that can be held differs. The transporting apparatus 11X (hereinafter referred to as transporting apparatus X) of FIG. 8(a) is for the rack 31 (for ten-sample rack) for holding ten test tubes 32, and the transporting apparatus 11W (hereinafter referred to as transporting apparatus W) of FIG. 8(b) is for the rack 31 (for five-sample rack) for holding five test tubes 32.

Figure 9A:
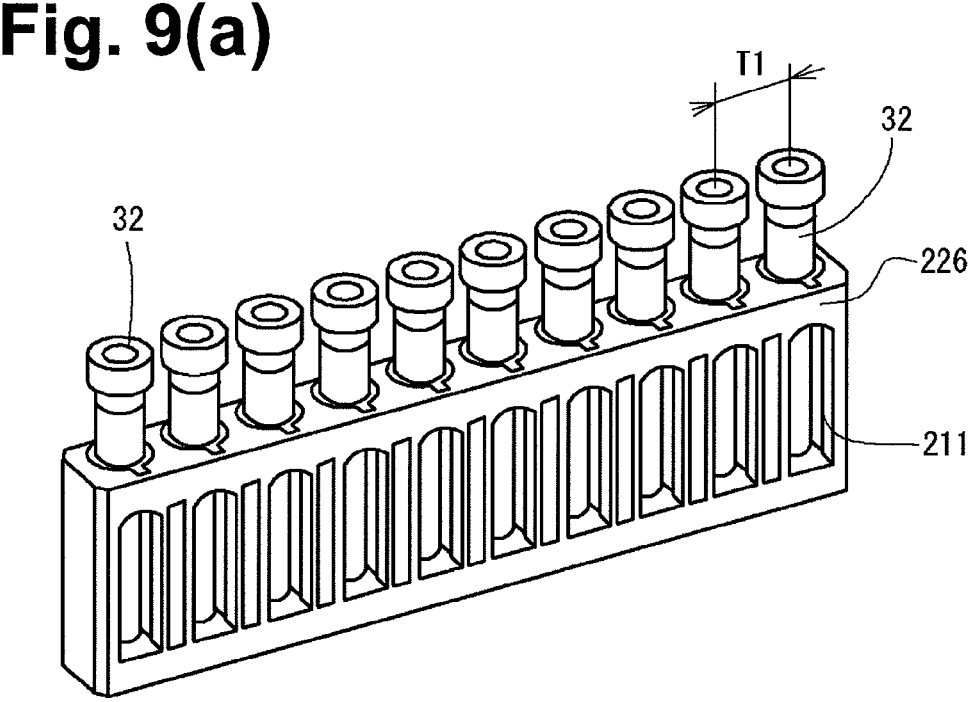
FIG. 9(a) is a perspective view showing a configuration of a ten-sample rack.
Figure 9B:
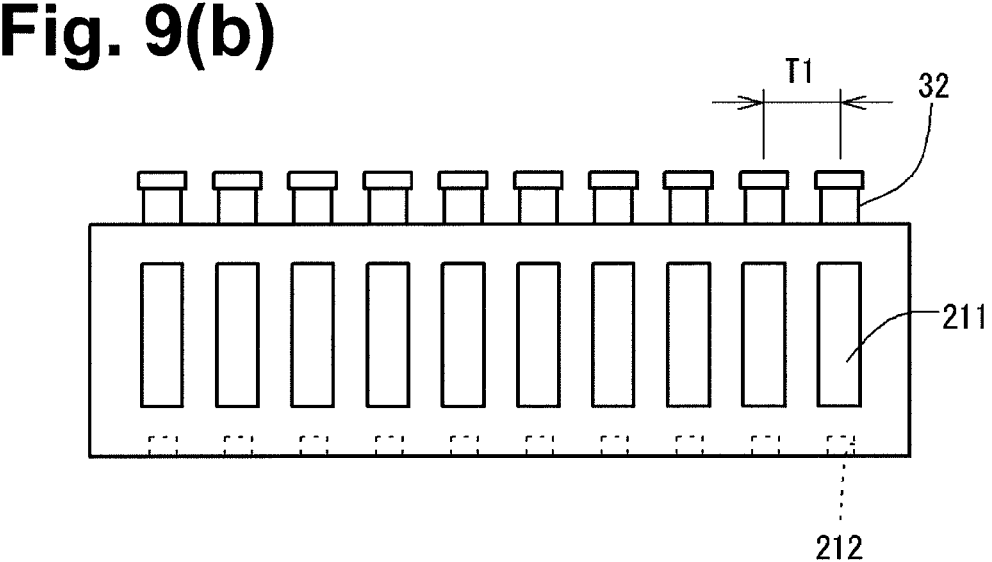
FIG. 9(b) is a front view showing the configuration of the ten-sample rack.
Figure 10:
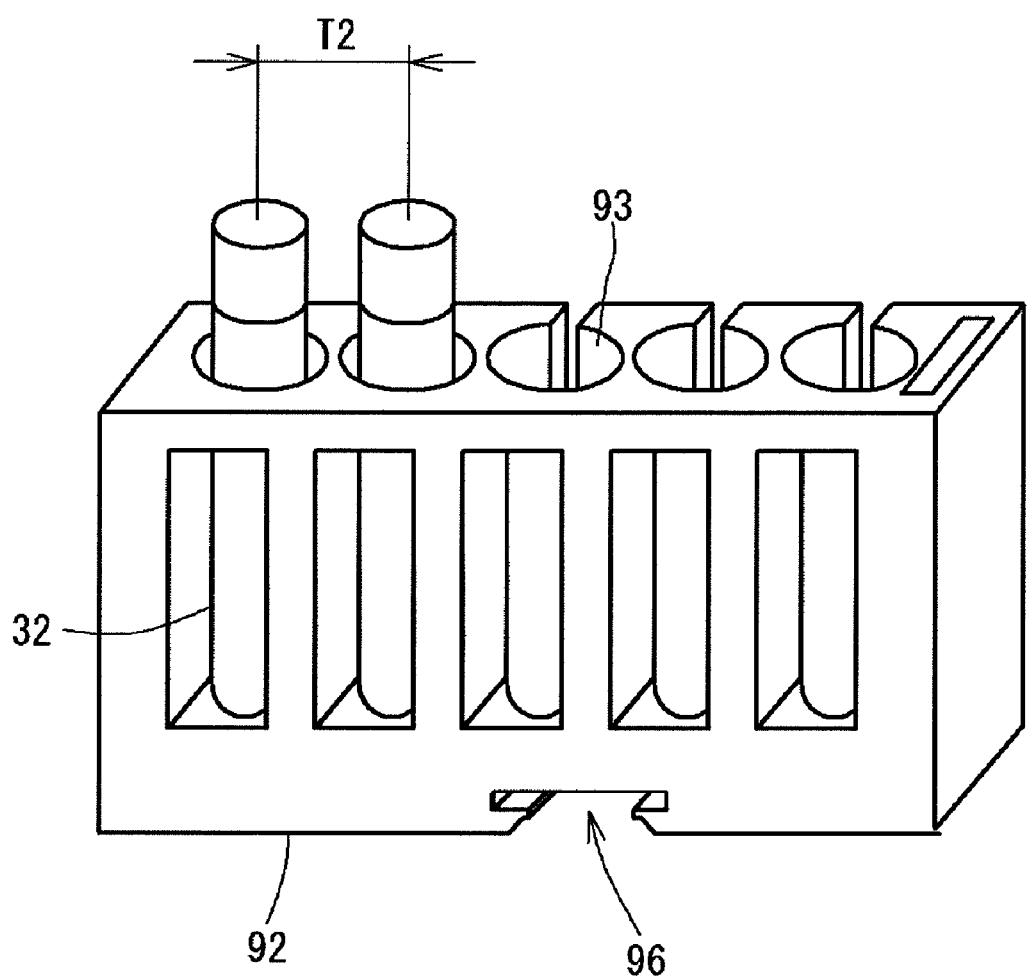
FIG. 10 is a perspective view showing a configuration of a five-sample rack.

The ten-sample rack used in the transporting apparatus X and the five-sample rack used in the transporting apparatus W will now be described. As shown in FIG. 9(a), the ten-sample rack 226 includes ten accommodating parts 211 for accommodating the test tube 32. As shown in FIG. 9(b), the ten-sample rack 226 includes ten concave parts 212 at the bottom surface. Each concave part 212 is arranged at a position corresponding to each accommodating part 211. As shown in FIG. 10, the five-sample rack 92 includes five accommodating parts 93 for accommodating the test tube 32 and one concave part 96 arranged at the center in the longitudinal direction of the bottom surface. The interval at which the accommodating position for accommodating the test tube 32 is arranged differs between the ten-sample rack 226 and the five-sample rack 92. That is, the distance T1 between the test tubes 32 accommodated in the accommodating part 211 of the ten-sample rack 226 and the distance T2 between the test tubes 32 accommodated in the accommodating part 93 of the five-sample rack 92 differ.

The transverse feeding operation for feeding the test tube 32 accommodated in the ten-sample rack 226 of the transporting apparatus X to the aspirating position facing the sample aspirating part 10a will now be described. The transporting apparatus X includes a projection for engaging the concave part 212 of the ten-sample rack 226, a slide mechanism for moving the projection, and a stepping motor for driving the slide mechanism (not shown). The transporting apparatus X is formed with a transport surface for transporting the ten-sample rack 226, so that the ten-sample rack 226 moves on the transport surface. A cutout for projecting the projection is formed at the transport surface. The projection is at an initial position of the lower part of the transport surface adjacent to the cutout. The projection moves from the initial position and projects out from the cutout when the stepping motor is operated. The projected projection engages one of the ten concave parts 212 arranged at the bottom surface of the ten-sample rack 226, and the projection horizontally moves and feeds the ten-sample rack 226 transversely by one pitch when the stepping motor is operated. The transporting apparatus X also provides a pulse signal of the number of pulse for feeding one pitch to the stepping motor in accordance with the distance T1 between the test tubes 32 of the rack 226, whereby the rack 226 is fed by one pitch. When the test tube 32 is transported to the aspirating position facing the sample aspirating part 10a, the sensor 37a detects such transport and transmits a detection signal to the measurement control unit 16 (see FIG. 3). The test tube 32 is then arranged at the aspirating position. The projection is then disengaged from the concave part 212, and returned to the initial position by operating the stepping motor. The projection then engages the adjacent concave part 21 of the previously engaged concave part 212, and the projection horizontally moves and feeds the ten-sample rack 226 transversely by one pitch when the stepping motor is operated.

The transverse feeding operation for feeding the test tube 32 accommodated in the five-sample rack 92 of the transporting apparatus W (FIG. 8(b)) to the aspirating position facing the sample aspirating part 10a will now be described. The transporting apparatus W includes a projection for engaging the concave part 96 of the five-sample rack 92, a movement belt for moving the projection, and a stepping motor for driving the movement belt (not shown). The transporting apparatus W is formed with a transport surface for transporting the five-sample rack 92, so that the five-sample rack 92 moves on the transport surface. A cutout for projecting the projection is formed at the transport surface. The projection is at an initial position of the lower part of the transport surface adjacent to the cutout. The projection moves from the initial position and projects out from the cutout when the stepping motor is operated. The projection engages one concave part 96 arranged at the bottom surface of the five-sample rack 92, and the projection horizontally moves and feeds the five-sample rack 92 transversely by one pitch when the stepping motor is operated. The transporting apparatus W also provides the number of pulse for feeding one pitch to the pulse motor in accordance with the distance T2 between the test tubes 32 of the rack 92, whereby the rack 92 is fed by one pitch. When the test tube 32 is transported to the aspirating position facing the sample aspirating part 10a, the sensor 37a detects such transport and transmits a detection signal to the measurement control unit 16 (see FIG. 3). The test tube 32 is then arranged at the aspirating position. When the stepping motor is operated while engaging the one concave part 96 arranged at the bottom surface of the five-sample rack 92, the projection horizontally moves and feeds the five-sample rack 92 transversely by one pitch. The projection is then disengaged from the concave part 96 when the five-sample rack 92 is fed by five pitches, and returned to the initial position by operating the stepping motor. The projection then engages the concave part 96 of the adjacent five-sample rack 92 of the five-sample rack 92 that has been transversely fed by five pitches, and horizontally moves and feeds the five-sample rack 92 transversely by one pitch when the stepping motor is operated.

As shown in FIG. 8, the transporting apparatus X for the ten-sample rack and the transporting apparatus W for the five-sample rack have substantially the same left-right width so as to correspond to the left-right width of the apparatus body 12 of the analyzer 10, but differs in the length in the front and back direction. The ten-sample rack transporting apparatus X and the five-sample rack transporting apparatus W differ in the transporting distance L11 and L12 of the rack 31 in the rack set region 34 and the rack accommodating region 35, and furthermore, the rack transporting distances L21 and L22 between the rack set region 34 and the rack accommodating region 35 as well as the feeding pitches P1 and P2 for feeding each test tube 32 to the aspirating position facing the sample aspirating part 10a differ. As described above, the mechanism and the operation for transverse feeding each test tube 32 to the aspirating position differ between the transporting apparatuses X, W. Therefore, programs for operation controlling the transporting apparatuses X, W differ from each other.

The transporting apparatus 11 also has a plurality of types depending on whether or not a control unit for controlling the operation thereof is arranged. As shown in FIG. 3, the transporting apparatuses X, W described above include a transport driving part 36a such as a stepping motor for transporting the rack 31 and a sensor 37a such as a photosensor and a microswitch for detecting the position etc. of the rack 31 but do not include a control unit. Thus a transporting apparatus X controlling program and a transporting apparatus W controlling program are incorporated in the memory 21 to control the transporting apparatuses X, W from the measurement control unit 16 of the analyzer 10.

When the transporting apparatus controlling program is executed, the signal from the transport sensor 37a is transmitted to the microprocessor 20 of the measurement control unit 16 via the sensor signal processing part 23 and the I/O controller 22. When the signal is transmitted, the microprocessor 20 transmits information for control to the driving unit control driver 24 via the I/O controller 22. The driving unit control driver 24 generates a control signal corresponding to the transmitted information, and transmits the control signal to the transport driving part 36a to perform the control. Therefore, communication of the sensor signal and the control signal is performed between the measurement control unit 16 and the transporting apparatuses X, W.

Figure 11:
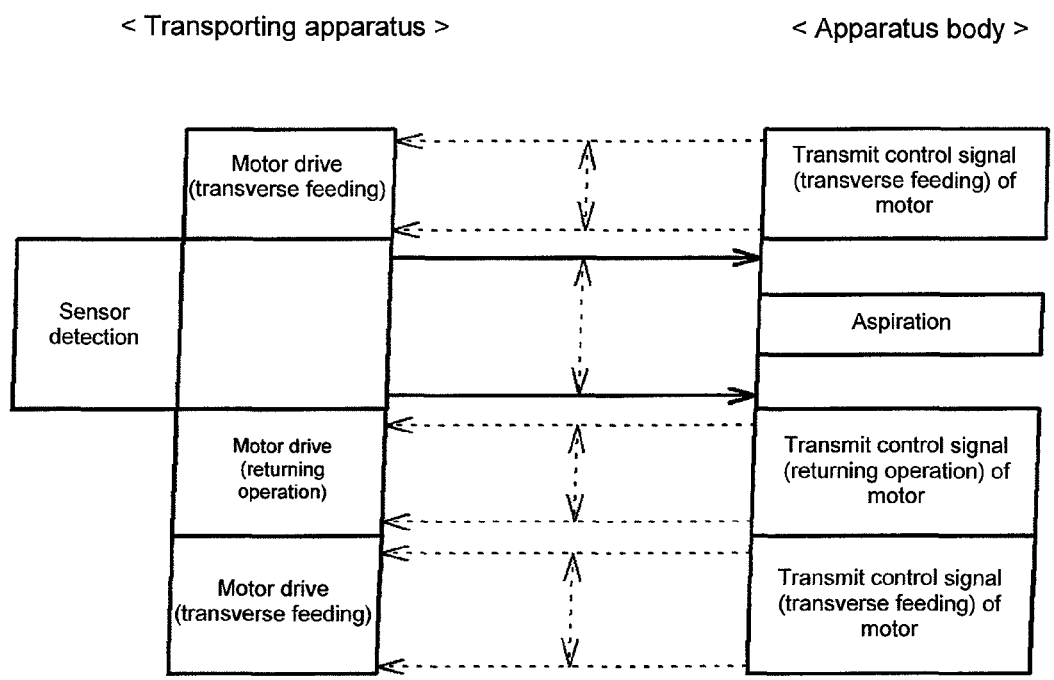
FIG. 11 is a timing chart showing a procedure for a communication between an apparatus body (measurement control unit) and the transporting apparatus X.

The procedure for the communication between the measurement control unit 16 and the transporting apparatus X (ten-sample rack transporting apparatus) will now be specifically described with reference to FIG. 11. The microprocessor 20 (FIG. 3) of the measurement control unit 16 executes the transporting apparatus X program stored in the memory 21. The microprocessor 20 provides information such as rotation amount, rotating direction, speed, and the like of the pulse motor for horizontally moving (transverse feeding) the projection for transporting the ten-sample rack 226 to the driving unit control driver 24. The driving unit control driver 24 transmits the control signal to the transport driving part 36a according to the received information. The transporting apparatus X receives the control signal, so that the transport driving part 36a operates according to the control signal, and the ten-sample rack 226 is transported (transversely fed) so that the test tube 32 at the head of the ten-sample rack 226 is at the aspirating position facing the sample aspirating part 10a. The sensor 37a of the transporting apparatus X detects that the head test tube 32 has been transported to the aspirating position facing the sample aspirating part 10a, and the detection signal is provided to the microprocessor 20 via the sensor signal processing part 23. The microprocessor 20 then controls the sample aspirating part 10a so that the sample is aspirated from the test tube 32. The sample aspirating part 10a then aspirates the sample from the test tube 32. When aspiration is terminated, the microprocessor 20 sends information such as rotation amount, rotating direction, speed, and the like of the pulse motor for performing the returning operation of returning the projection for transporting the ten-sample rack 226 to the initial position to the driving unit control driver 24. The driving unit control driver 24 transmits the control signal to the transport driving part 36a according to the received information. The transporting apparatus X receives the control signal, so that the transport driving part 36a operates according to the control signal and the projection is returned to the initial position. Such procedure is repeatedly carried out for all the test tubes 32 accommodated in the ten-sample rack 226.

The configuration of transporting apparatuses Y, Z will now be described. As shown in FIG. 3, the transporting apparatuses Y, Z include a transport driving part 36b and a transport sensor 37b. The transporting apparatuses Y, Z also include a control unit 38. The control unit 38 is arranged with an external communication controller 39, a microprocessor 40, and a memory 41. The external communication controller 39 is connected to the external communication controller 25 of the analyzer 10. When the transporting apparatuses Y, Z are connected, a communication program for communicating with the control units 38 of the transporting apparatuses Y, Z is executed in the measurement control unit 16 of the analyzer 10 to achieve cooperation of operation with the transporting apparatuses Y, Z. The transporting apparatuses Y, Z is generally used as one part of a transport system used for a plurality of analyzers in a large facility etc. The transport driving part 36b is operation controlled by a control program incorporated in the memory 41 of the control unit 38.

When the transporting apparatuses Y, Z are connected to the analyzer 10, the communication is performed in the following manner. For example, when the transporting apparatus Y, Z transports the test tube 32 to the aspirating position facing the sample aspirating part 10a, the information indicating the same is transmitted to the analyzer 10, and the analyzer 10 receives such information and performs the operation of aspirating the sample from the test tube 32. Subsequently, the analyzer 10 transmits information indicating that the sample has been aspirated to the transporting apparatus Y, Z, and the transporting apparatus Y, Z receives such information and performs the operation of transporting the next test tube 32 to the aspirating position facing the sample aspirating part 10a.

Figure 12:
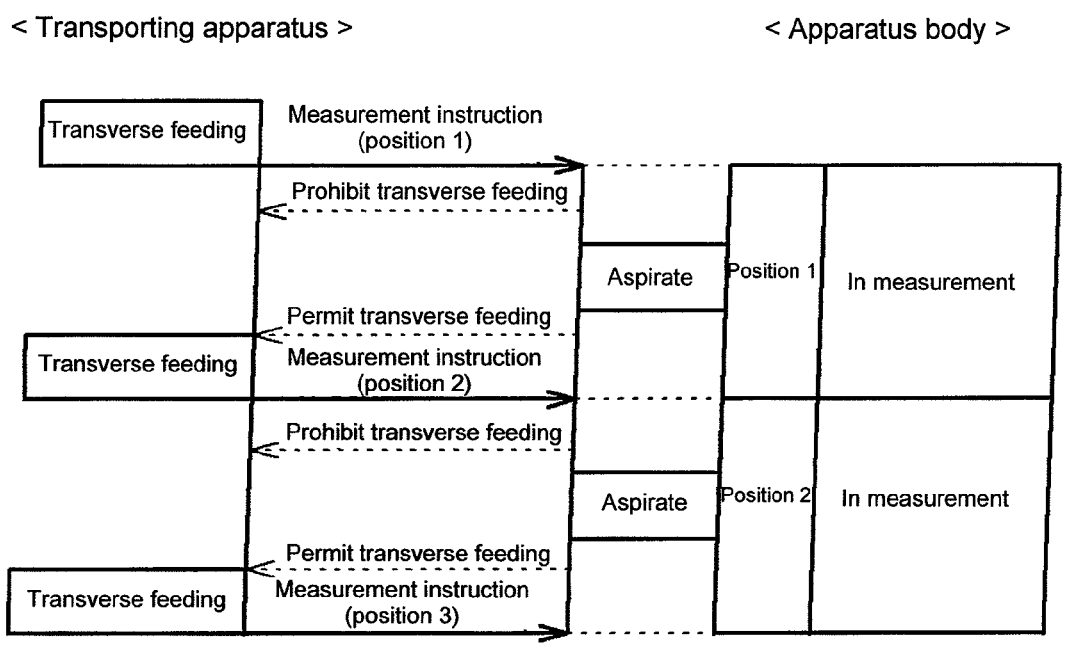
FIG. 12 is a timing chart showing a procedure for a communication between the apparatus body (measurement control unit) and the transporting apparatus Y.

The procedure for communication between the transporting apparatus Y (ten-sample rack transporting apparatus) and the analyzer 10 will now be specifically described with reference to FIG. 12. The microprocessor 40 of the transporting apparatus Y executes the control program for controlling the operation of the transporting apparatus Y, and the microprocessor 20 of the apparatus body 12 executes the communication program for performing communication of the analyzer 10 and the transporting apparatus Y and the control program for controlling the operation of the analyzer 10. The microprocessor 40 of the transporting apparatus Y transports (feeds transversely) the ten sample rack 226 so that the head test tube 32 of the sample rack 226 comes to the aspirating position facing the sample aspirating part 10a. The microprocessor 40 sends a measurement instruction signal instructing the start of measurement of the apparatus body 12 (or transport terminated signal indicating that transport is terminated) to the measurement control unit 16 of the analyzer 10. The microprocessor 20 of the apparatus body 12 receives the measurement instruction signal, and sends a prohibiting signal indicating the prohibition of the transverse feeding operation of the ten-sample rack 226 to the control unit 38 of the transporting apparatus Y. After transmitting the prohibiting information, the microprocessor 20 of the apparatus body 12 performs the operation of aspirating the sample from the test tube 32 (position 1) of the ten-sample rack 226 transversely fed to the aspirating position facing the sample aspirating part 10a. When the aspirating operation is terminated, the microprocessor 20 sends a permitting signal indicating permission of transverse feeding operation of the ten-sample rack 226 (or aspirate terminated signal indicating that aspirating operation is terminated) to the control unit 38 of the transporting apparatus Y. The microprocessor 40 of the transporting apparatus Y feeds the ten-sample rack 226 transversely so that the next test tube 32 (position 2) of the ten-sample rack 226 comes to the aspirating position facing the sample aspirating part 10a. Thereafter, the microprocessor 40 sends information on the measurement instruction to the measurement control unit 16. Such procedure is repeatedly performed for all the test tubes 32 accommodated in the ten-sample rack 226.

In the analyzer 10 of the present invention, all of the control program and the communication program (hereinafter collectively referred to as transporting apparatus program) corresponding to the type (X, Y, Z, W) of the transporting apparatus 11 as described above are incorporated in advance in the memory 21 of the measurement control unit 16. The analyzer 10 obtains the identification information indicating the type (X, Y, Z, W) of the connected transporting apparatus 11, and selects and executes the transporting apparatus program according to the identification information. The operation corresponding to any of the plurality of types of transporting apparatus 11 can then be performed.

That is, the analyzer 10 of the present invention includes an input means for inputting identification information for identifying the type of the transporting apparatus 11, and a control unit 16 for performing the operation (control or communication) with respect to the transporting apparatus 11 according to the identification information input by the input means.

In the present embodiment, the analyzer 10 has a configuration of inputting the identification information corresponding to the type (X, Y, Z, W) of the transporting apparatus 11 manually by the user through the input part 29 of the system controller (personal computer) 13, and selecting the transporting apparatus program to be executed by the measurement control unit 16 according to the input identification information.

Figure 13:
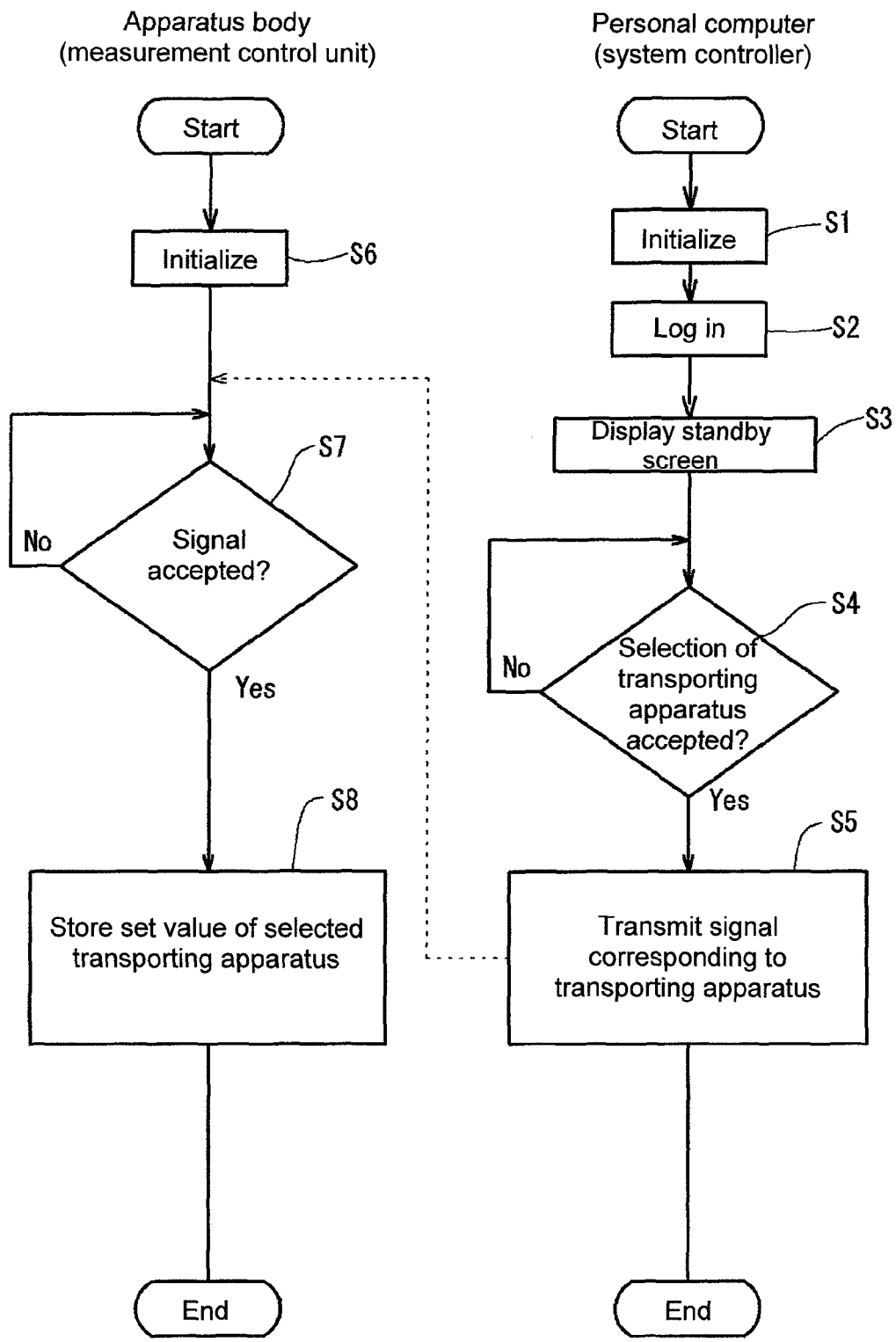
FIG. 13 is a flowchart showing a procedure for setting set value of the transporting apparatus when the transporting apparatus is connected to the analyzer.

FIG. 13 is a flowchart showing the procedures for setting the set value of each transporting apparatus X, Y, Z when the transporting apparatus 11 is connected to the analyzer 10. When the power (not shown) of the apparatus body 12 is turned ON, initialization of the measurement control unit 16 (initialization of the program) is performed in step S6, the operation check of each unit of the apparatus body 12 is performed, and the standby state is obtained. When the power (not shown) of the system controller 13 (personal computer) is turned ON, initialization of the system controller 13 (initialization of the program) is performed in step S1, and the log-in screen is displayed on the display 28. In the log-in screen, the user having the authority to set the transporting apparatus logs in (step S2), and the service icon for setting the transporting apparatus is displayed as hereinafter described. In step S3, the system controller 13 displays the standby screen (hereinafter described as operation screen W1).

As shown in FIGS. 14 to 17, the operation screens W1 to W4 includes a title bar B1, a menu bar B2, a tool bar B3, a function display region R, and a status bar B4. The title bar B1 displays name etc. of the operation screen W1 to W4, and the menu bar B2 displays the operation menu in the operation screen W1 to W4. The tool bar B3 displays a plurality of tool buttons (icons) TIC for executing various functions.

Figure 14:
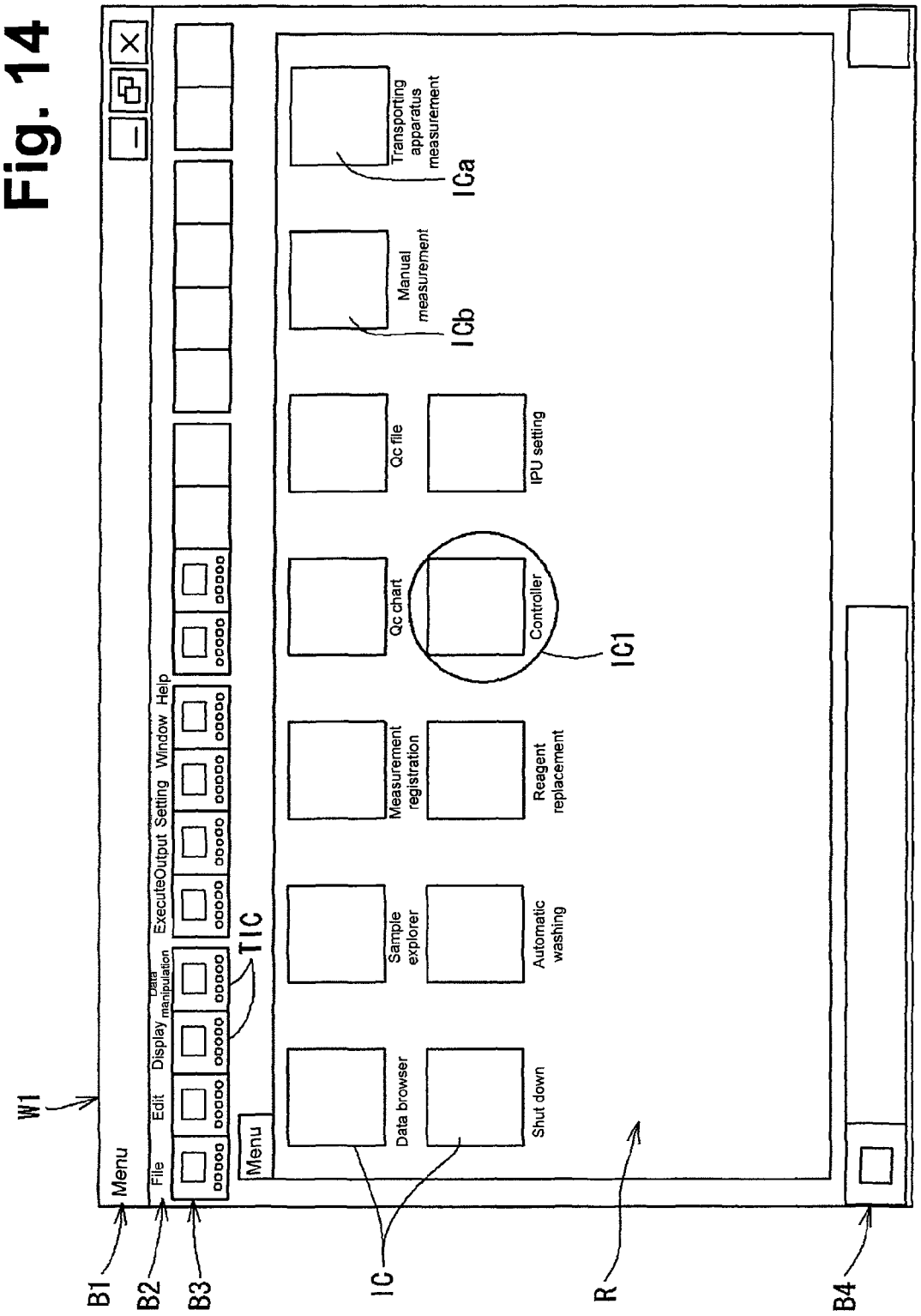
FIG. 14 is a frame format view of a display screen (menu screen) of the operation program according to the first embodiment of the present invention.

FIG. 14 shows the menu screen W1 of the operation program, and a plurality of function icons IC is displayed in the function display region R of the menu screen W1. Various measurements, settings, and the like are executed by selecting one of the function icons IC.

A controller icon IC1 of the menu screen W1 is selected to identify the type of transporting apparatus 11 connected to the analyzer 10.

Figure 15:
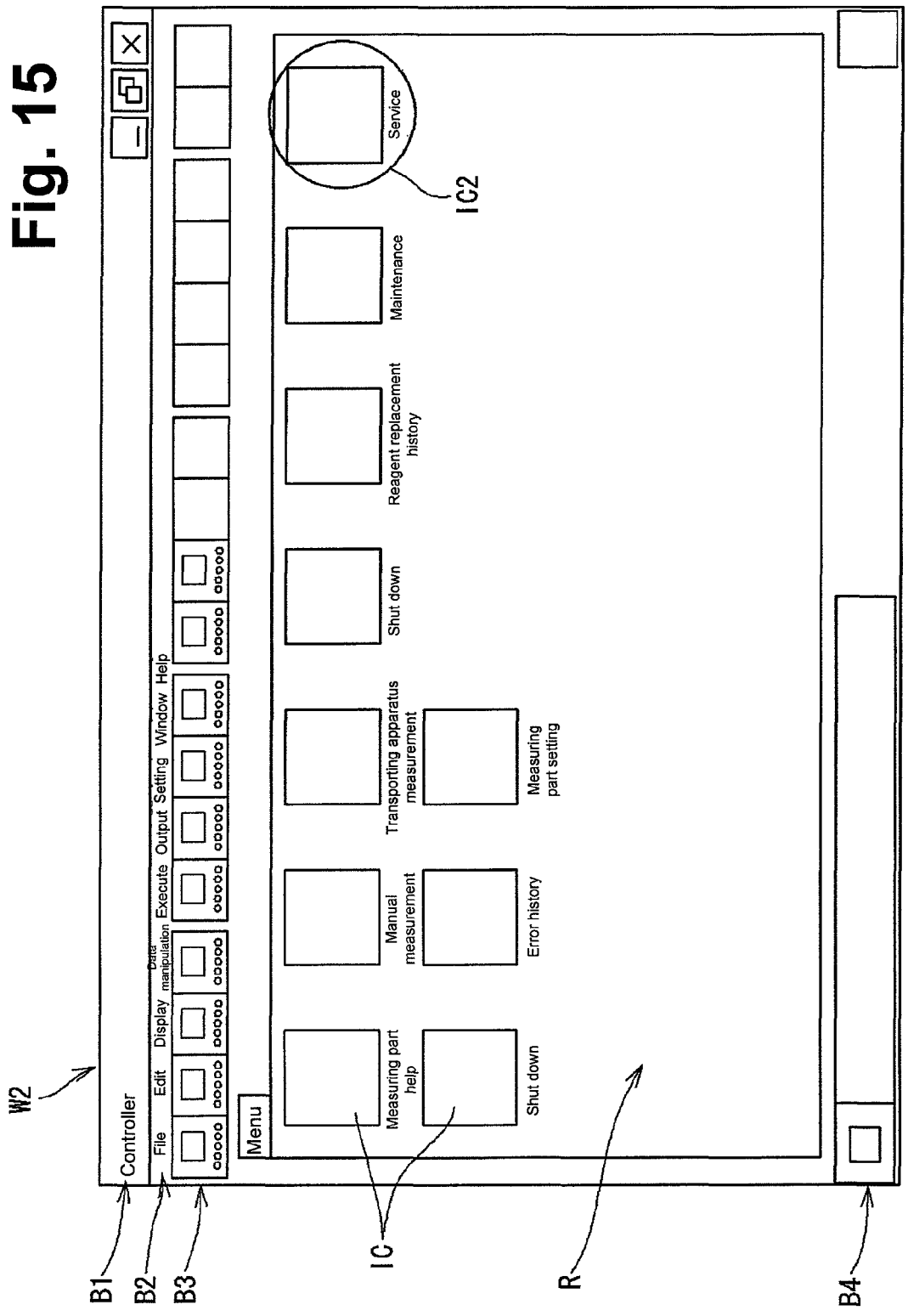
FIG. 15 is a configuration view of a display screen (controller screen) of the operation program.

FIG. 15 shows a controller screen W2 displayed when the controller icon IC1 (FIG. 14) is selected. A service icon IC2 is displayed in the function display region R of the controller screen W2. The service icon IC2 is an icon for calling up the function (service function) used in the installation of the analyzer 10 or the maintenance after the installation.

The service icon IC2 is displayed only when the user ID and the password input when operating the operation program and the operating system is recognized as those of a specific person. In other words, only the person having the authority to use the service function can use the function. Therefore, the service icon IC2 will not be displayed even if the user other than the person having the authority to use the service function logs into the system controller 13 and displays the controller screen W2. Thus, there is no possibility the setting of the service function will be changed etc. by the user by mistake.

Figure 16:
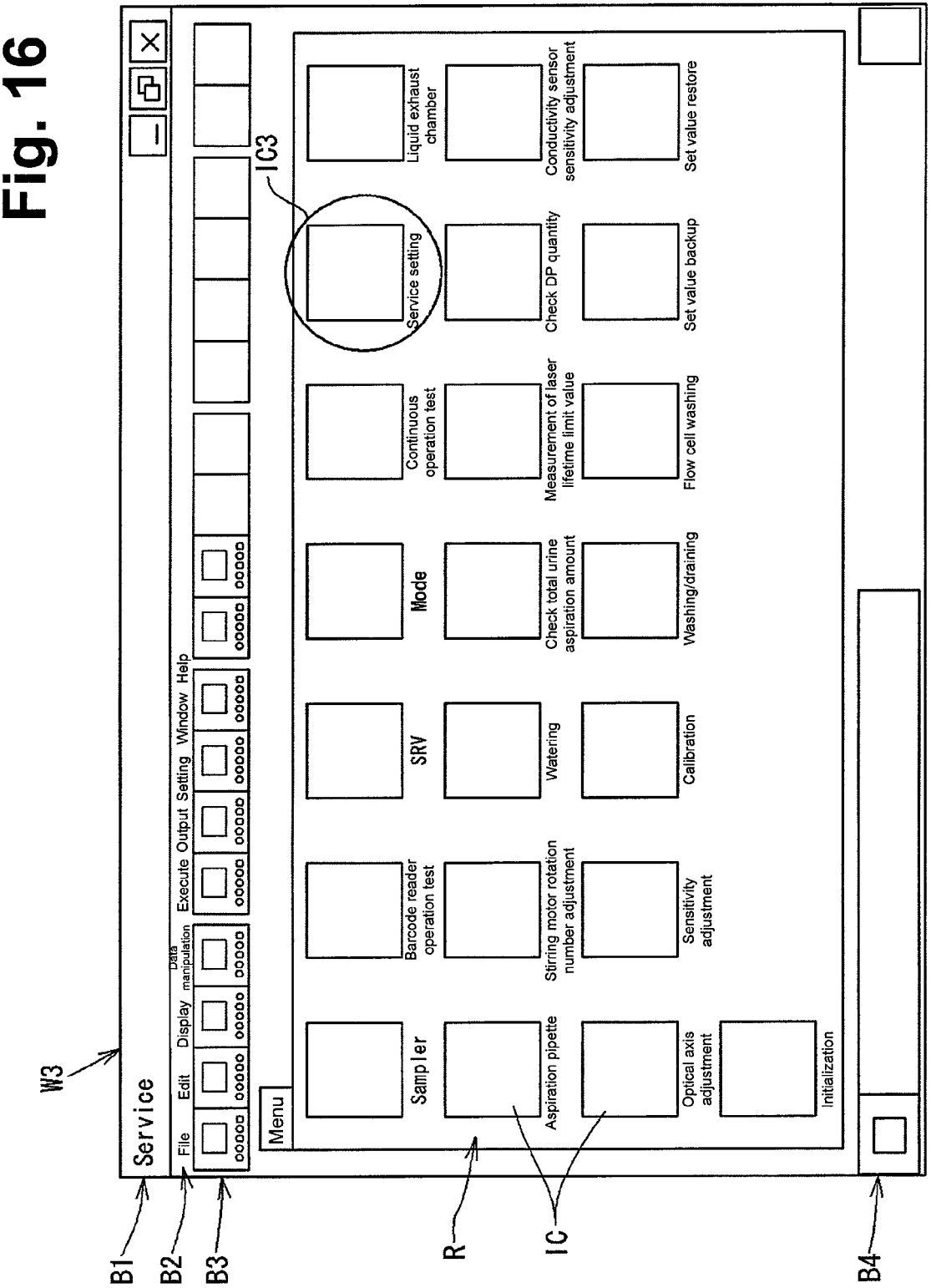
FIG. 16 is a configuration view of a display screen (service screen) of the operation program.

FIG. 16 shows a service screen W3 displayed when the service icon IC2 (FIG. 15) is selected. The function icons IC related to various settings, tests, and maintenances are displayed in the function display region R of the service screen W3. The service setting icon IC3 of the service screen W3 is selected to identify the transporting apparatus 11 connected to the analyzer 10.

Figure 17:
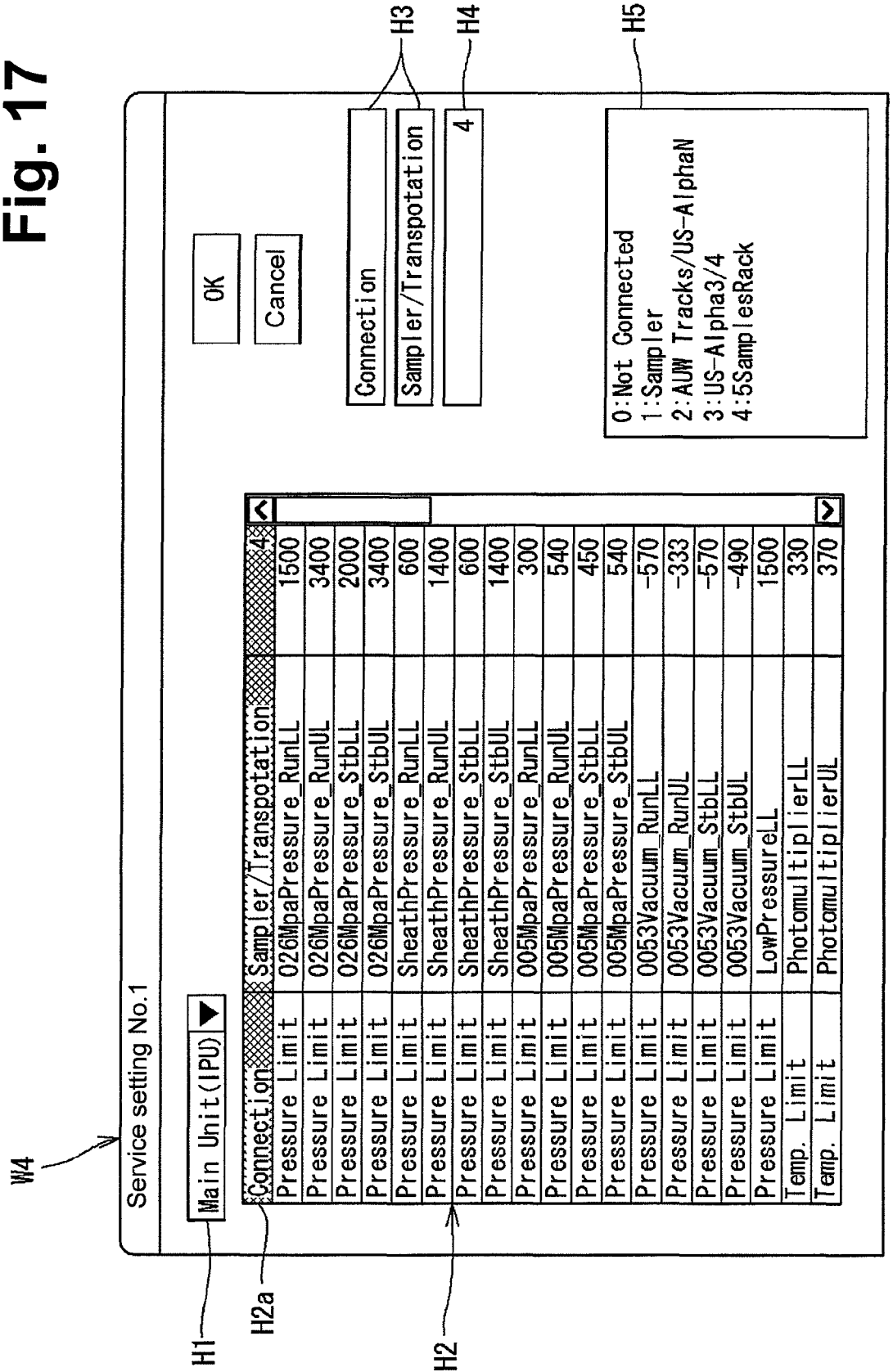
FIG. 17 is a configuration view of a display screen (service setting screen) of the operation program.

FIG. 17 is a service setting screen W4 displayed when the service setting icon IC3 (FIG. 16) is selected. A pull-down menu H1 for selecting the target of service setting, an item display window H2 for displaying setting items of the selected target, a selected item display part H3 for displaying the items selected in the item display window H2, an input field H4 for inputting the set values which are identification information of the transporting apparatus 11, and a set value display part H5 showing an example of a set value that can be input to the input field H4.

Various setting items are listed in the up and down direction in the item display window H2, and one of the items is a connection setting item (connection, sampler/transportation) H2a of the transporting apparatus 11. When the item H2a is selected, the relevant item name is displayed in the selected item display part H3. One of the set values displayed on the set value display part H5 can be input to the input field H4. In the present example, the set value of one of "0" to "4" can be input. Specific names etc. of the transporting apparatus 11 to be connected are displayed next to each set value "0" to "4" in the set value display part H5.

The relationship between the type (X, Y, Z, W) of the transporting apparatus 11 connected to the analyzer 10 and the set values "0" to "4" is as shown in FIG. 18. The set value "0" is the set value of "standard mode" selected when the transporting apparatus 11 is not connected to the analyzer 10. In this case, only manual measurement of supplying the sample to the analyzer 10 by hand can be performed.

The set value "1" is the set value of "transporting apparatus X mode" selected when the transporting apparatus 11 (transporting apparatus X shown in FIG. 8(a)) for the ten-sample rack is connected to the analyzer 10. The transporting apparatus X does not have a control unit, and is controlled by the measurement control unit 16 (FIG. 3) of the analyzer 10.

The set value "2" is the set value of "transporting apparatus Y mode" selected when the transporting apparatus 11 (Y) including the control unit 38 (FIG. 3) is connected to the analyzer 10. The set value "3" is the set value of "transporting apparatus Z mode" selected when the transporting apparatus 11 (Z) including the control unit 38 (FIG. 3) different from the transporting apparatus Y is connected to the analyzer 10.

The set value "4" is the set value of "transporting apparatus W mode" selected when the transporting apparatus 11 (transporting apparatus W shown in FIG. 8(b)) for the five-sample rack is connected to the analyzer 10. The transporting apparatus W does not have a control unit, and is controlled by the measurement control unit 16 (FIG. 3) of the analyzer 10. Therefore, in the present embodiment, the operation program to be executed by the system controller 13, the input part 29, and the like configure the input means for inputting the identification information of the transporting apparatus 11.

Returning to the flowchart shown in FIG. 13, the continuation of the procedure for setting the set values of the transporting apparatus will be described. In step S4, the system controller 13 determines whether or not the selection of the transporting apparatus is accepted, that is, whether or not the input of the set value "0" to "4" is made from the operation program of the system controller 13 as described above. If the set value is input, the system controller 13 transmits a signal corresponding to the relevant transporting apparatus to the measurement control unit 16 of the apparatus body 12 (step S5). The measurement control unit 16 determines whether or not the signal corresponding to the transporting apparatus is received (step S7), and if the relevant signal is received, stores the set value of the transporting apparatus corresponding to the signal in the memory 21 and terminates the process (step S8).

When the transporting apparatus 11 is connected to the analyzer 10, the measurement (manual measurement mode) for supplying the sample by hand without using the transporting apparatus 11 can be selectively carried out in addition to the measurement (transporting apparatus measurement mode) using the transporting apparatus 11. Specifically, as shown in FIG. 14, such measurements can be performed by selecting the transporting apparatus measurement icon ICa or the manual measurement icon ICb from the menu screen W1 displayed on the display 28 of the system controller (personal computer) 13.

FIG. 19 is a flowchart showing the procedures of when the analyzer 10 connected with the transporting apparatus 11 performs the transporting apparatus measurement mode. First, when the power (not shown) of the apparatus body 12 is turned ON, initialization of the measurement control unit 16 (initialization of the program) is performed in step S41, and the operation check of each unit of the apparatus body 12 is performed. The standby display is obtained when the indicator 6 shown in FIG. 1 is lighted green (step S42). When the power (not shown) of the system controller 13 (personal computer) is turned ON, the initialization of the system controller 13 (initialization of the program) is performed in step S61, and thereafter, the standby screen (menu screen W1: see FIG. 14) is displayed on the display 28 (step S62).

In step S63, when the user selects the transporting apparatus ICa of the standby screen (menu screen W1) displayed on the display 28, the system controller 13 transmits the measurement start signal to the measurement control unit 16 of the apparatus body 12 (step S64).

The measurement control unit 16 of the apparatus body 12 determines whether or not the start signal is received in step S43, and when the measurement start signal is received, reads out the transporting apparatus measurement program from the memory 21 in step S44, and reads out the transporting apparatus set value from the memory 21 (step S45). In step S46, the measurement control unit 16 determines what the transporting apparatus set value is (step S46). The measurement control unit 16 executes the transporting apparatus X program when the set value is "1", (step S47a), executes the transporting apparatus Y program when the set value is "2" (step S47b), executes the transporting apparatus Z program when the set value is "3" (Step S47c), and executes the transporting apparatus W program when the set value is "4" (step S47d).

In step S48, the measurement control unit 16 transmits an operation state signal indicating that the apparatus body 12 is in the operation state to the system controller 13, and lights the indicator 6 shown in FIG. 1 to orange to indicate that the apparatus body 12 is in operation (step S49). In step S50, the measurement control unit 16 determines whether or not the measurement is completed, and returns the process to step S49 if the measurement is not completed. If the measurement is completed, the measurement control unit 16 transmits the measurement completed signal to the system controller 13 in step S51, and returns the process to step S42.

In step S65, the system controller 13 determines whether or not the operation state signal is received, and if the operation state signal is received, displays the display indicating "in measurement operation" on the display 28 (step S66). If the operation state signal is not received in step S65, the system controller 13 returns the process to step S62. The system controller 13 determines whether or not the measurement completed signal is received in step S67, and if the measurement completed signal is received, returns the process to step S62, and if the measurement completed signal is not received, returns the process to step S66.

If the instruction of measurement start is not made in step S63, the system controller 13 determines whether or not the instruction of shutdown is received in step S68. If the instruction of shutdown is not received in step S68, the system controller 13 returns the process to step S62. If the instruction of shutdown is received in step S68, the system controller 13 transmits a shutdown signal to the measurement control unit 16 (step S69).

If the measurement start signal is not received in step S43, the measurement control unit 16 determines whether or not the shutdown signal is received in step S52. If the shutdown signal is not received in step S52, the measurement control unit 16 returns the process to step S42. If the shutdown signal is received in step S52, the control unit 16 executes shutdown in step S53, and transmits a shutdown completed signal to the system controller 13 (step S54), and terminates the process.

The system controller 31 determines whether or not the shutdown completed signal is received in step S70, and repeats the process until the shutdown completed signal is received.

The transporting apparatus program includes a plurality of modules (components of program), that is, a common module common to all the transporting apparatus 11, and a dedicated module used according to each transporting apparatus. The measurement control unit 16 activates the common module, and selectively activates the dedicated module corresponding to the connected transporting apparatus to cause each transporting apparatus to perform the operation.

As described above, in the present embodiment, the transporting apparatus program corresponding to a plurality of types (X, Y, Z, W) of transporting apparatus 11 is stored in advance in the measurement control unit 16 of the analyzer 10, and the transporting apparatus program corresponding to the input identification information of the transporting apparatus 11 is executed by the measurement control unit 16. Thus, when the transporting apparatuses 11X, 11Y, 11W are connected to the analyzer 10, the transporting apparatus program corresponding to the type of the connected transporting apparatus does not need to be incorporated in the analyzer 10. Therefore, the setting task etc. involved in the connection of the transporting apparatus 11 can be simplified.

When the transporting apparatus 11 is equipped with the control unit, the communication program with the transporting apparatus 11 is executed, and when the transporting apparatus 11 is not equipped with the control unit, the control program of the transporting apparatus 11 is executed, whereby an appropriate operation can be performed on various types of transporting apparatuses 11.

The identification information of the transporting apparatus 11 is easily input from the input part 29 of the system controller 13. Furthermore, the input of the identification information by the input part 29 is made only by the person having the input authority, and the input by other users etc. is regulated, whereby false operation involved in the input of false identification information is prevented.

Second Embodiment

Figure 20:
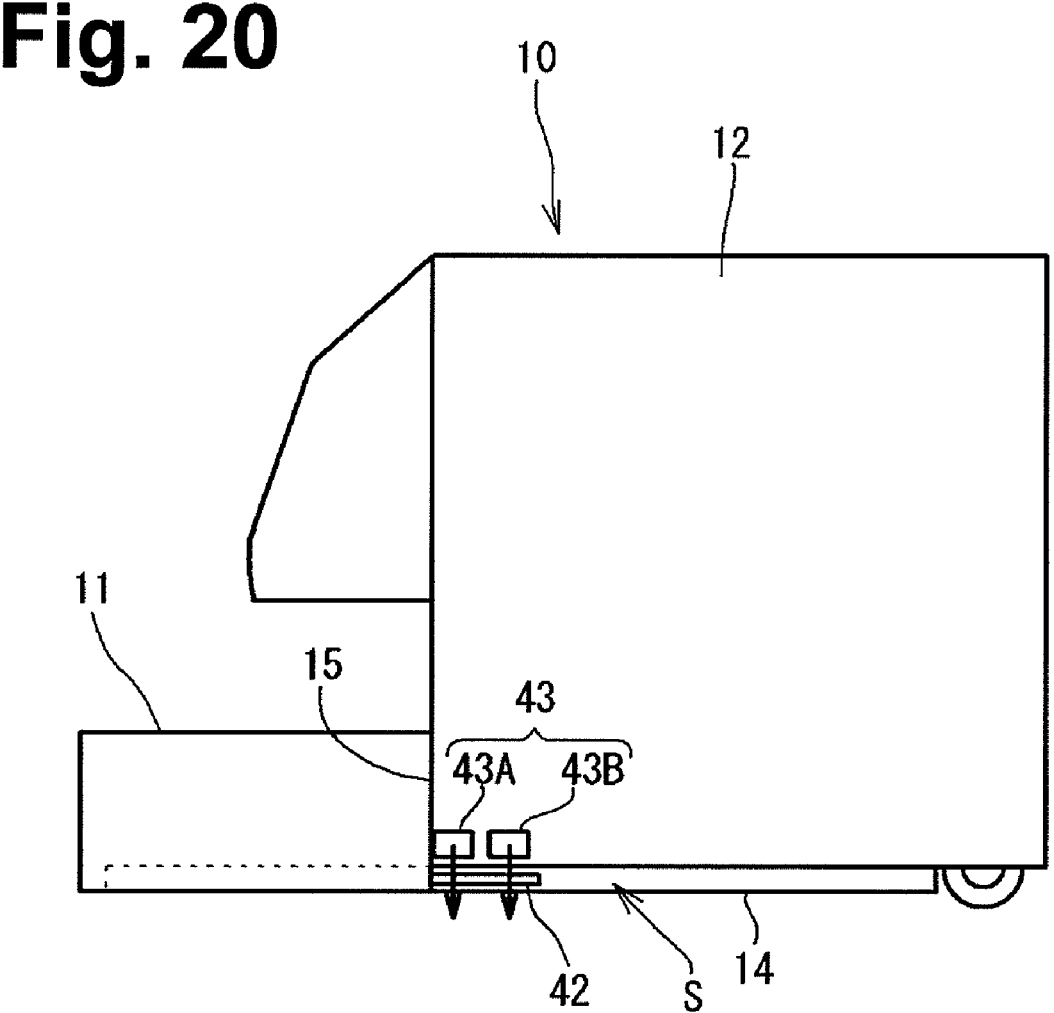
FIG. 20 is a schematic side view showing a state in which the transporting apparatus is connected to the analyzer according to a second embodiment of the present invention.

The second embodiment of the present invention will now be described. As shown in FIG. 20, in the second embodiment, an identifying part 42 including the identification information for identifying the type is arranged in each transporting apparatus 11, and detection means 43 for detecting the identifying part 42 is arranged in the analyzer 10. The detection means 43 includes detection sensors 43A, 43B made of optical sensor, and the identifying part 42 is configured by a light shielding plate for light shielding the detection sensor 43.

The light shielding plate 42 is arranged in a projecting manner at the lower back part of the transporting apparatus 11, that is, a connection part to be connected with the apparatus body 12 of the analyzer 10. When the transporting apparatus 11 is connected to the apparatus body 12 of the analyzer 10, the light shielding plate 42 is inserted to the lower side (space S formed by supporting leg 14) of the apparatus body 12. The detection sensors 43A, 43B are arranged at the lower front part of the apparatus body 12, that is, the connection part 15 with respect to the transporting apparatus 11, so that the inserted light shielding plate 42 can be detected.

Figure 21A:
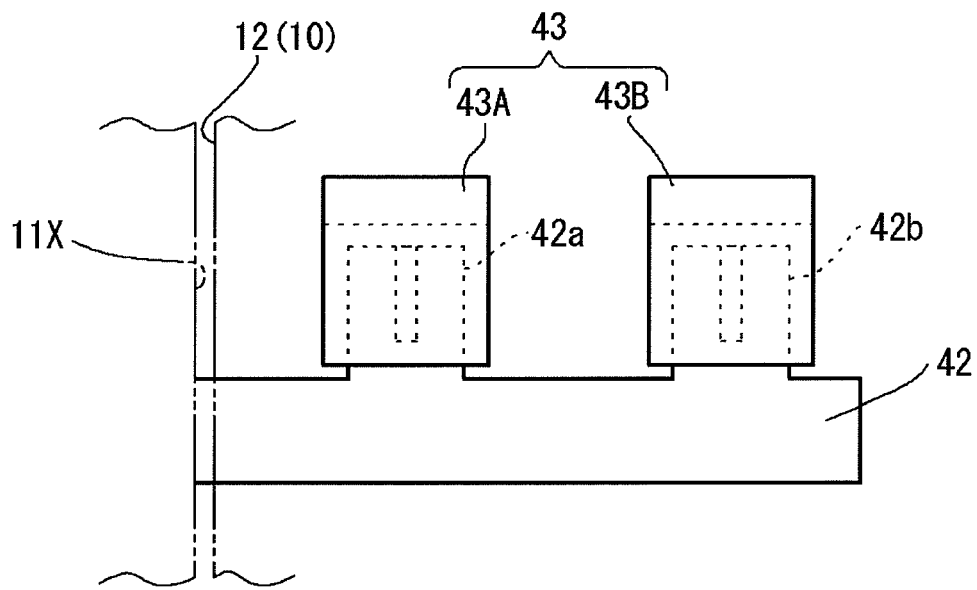
FIG. 21(a) is an explanatory view showing a detection means and an identifying part for identifying the transporting apparatus X.
Figure 21B:
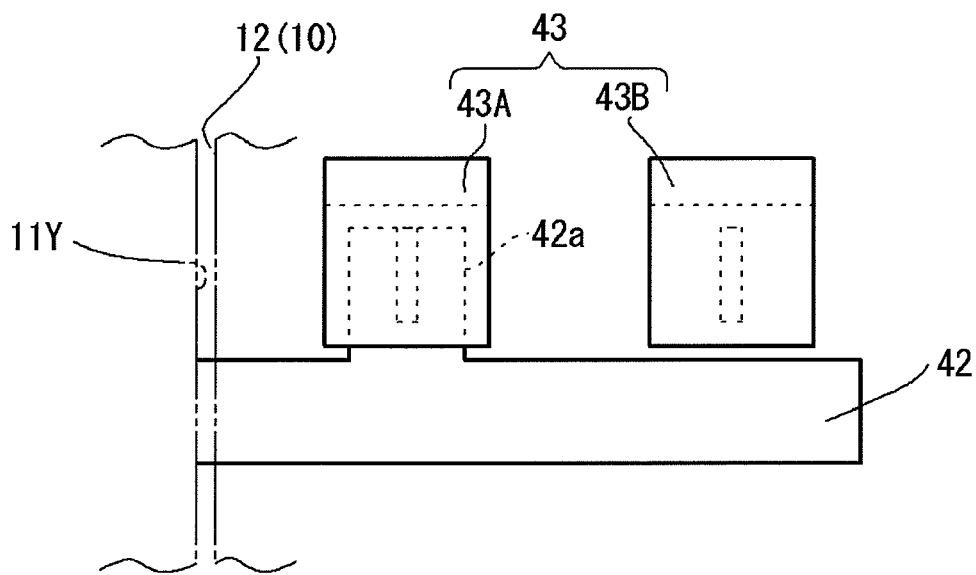
FIG. 21(b) is an explanatory view showing a detection means and an identifying part for identifying the transporting apparatus Y.
Figure 21C:
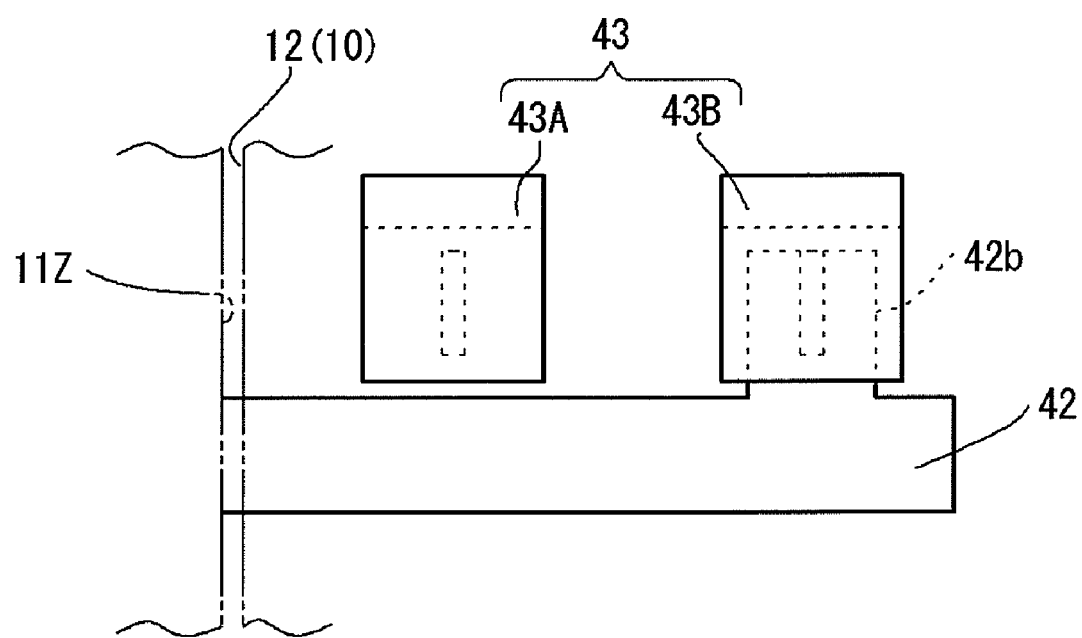
FIG. 21(c) is an explanatory view showing a detection means and an identifying part for identifying the transporting apparatus Z.

FIG. 21 is an explanatory view showing a relationship between the detection sensors 43A, 43B and the light shielding plate 42. In the present embodiment, four patterns of when three types of transporting apparatus 11 are connected and when the transporting apparatus 11 is not connected are identifiable. Specifically, two detection sensors (first, second sensors) 43A, 43B are arranged in the analyzer 10, and the light shielding plate 42 as shown in FIGS. 21(a) to 21(c) is arranged in each transporting apparatus 11. In the second embodiment, three types of X, Y, and Z are identified of the four types X, Y, Z, W (see FIG. 3 and FIG. 18) of transporting apparatuses 11 described in the first embodiment.

Two light shielding parts 42a, 42b for light shielding the detection sensors 43A, 43B are arranged in the light shielding plate 42 of the transporting apparatus X of FIG. 21(a). One light shielding part 42a for shielding only the first detection sensor 43A is arranged in the light shielding plate 42 of the transporting apparatus Y of FIG. 21(b), and one light shielding part 42b for light shielding only the second detection sensor 42B is arranged in the light shielding plate 42 of the transporting apparatus Z of FIG. 21(c).

The relationship between the type (X, Y, Z) of the transporting apparatus 11 connected to the analyzer 10 and the state and output of the first and second detection sensors 43A, 43B is as shown in FIG. 22. According to FIG. 22, when the transporting apparatus X is connected to the analyzer 10, both the first and second detection sensors 43A, 43B are light shielded (state of FIG. 21(a)), and both output becomes Low level. When the transporting apparatus Y is connected, the first detection sensor 43A is light shielded and the output thereof becomes Low level, but the second detection sensor 43B is not light shielded and is in an light incident state, and thus the output thereof becomes High level (state of FIG. 32(b)). When the transporting apparatus Z is connected, the second detection sensor 43B is light shielded and the output thereof becomes Low level, but the first detection sensor 43A is not light shielded and is in an light incident state, and thus the output thereof becomes High level (state of FIG. 32(c)). When the transporting apparatus is not connected, both the first and second detection sensors 43A, 43B are not light shielded and are in an light incident state, and thus both output becomes High level.

Therefore, the combination of the outputs of the first and second detection sensors 43A, 43B differ depending on which transporting apparatus X, Y, Z to connect to the analyzer 10, and thus the type of the connected transporting apparatus 11 can be recognized by determining the combination of the outputs.

Figure 23:
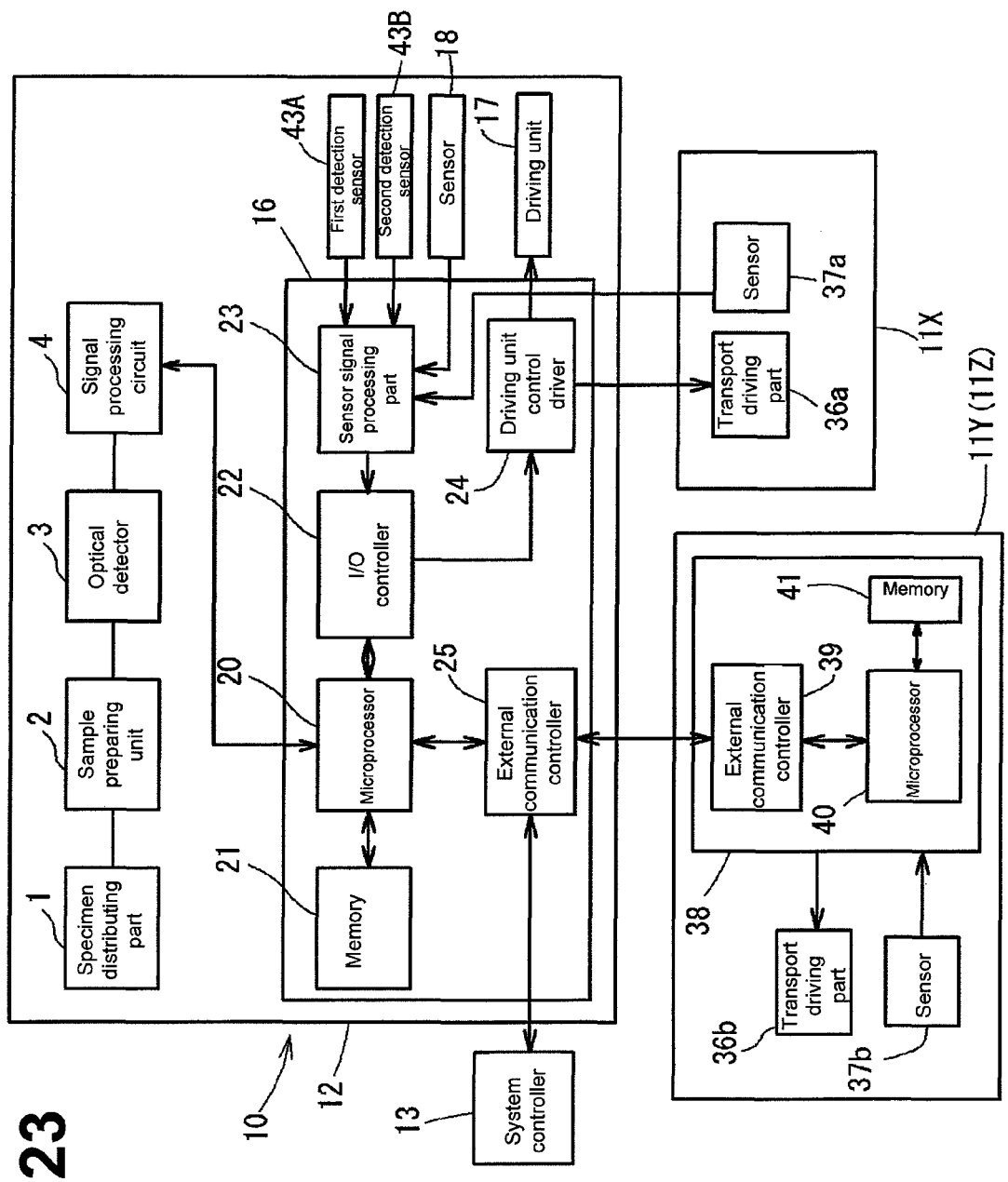
FIG. 23 is a block diagram of the analyzer and the transporting apparatus according to the second embodiment of the present invention.

As shown in FIG. 23, the first and second detection sensors 43A, 43B are arranged in the apparatus body 12 of the analyzer 10. Configurations other than the first and second detection sensors 43A, 43B are the same as the configuration shown in FIG. 3, and thus the description thereof will be omitted. The output signals of the first and second detection sensors 43A, 43B are transmitted to the microprocessor 20 via the sensor signal processing part 23 and the I/O controller 22 of the measurement control unit 16.

Figure 24:
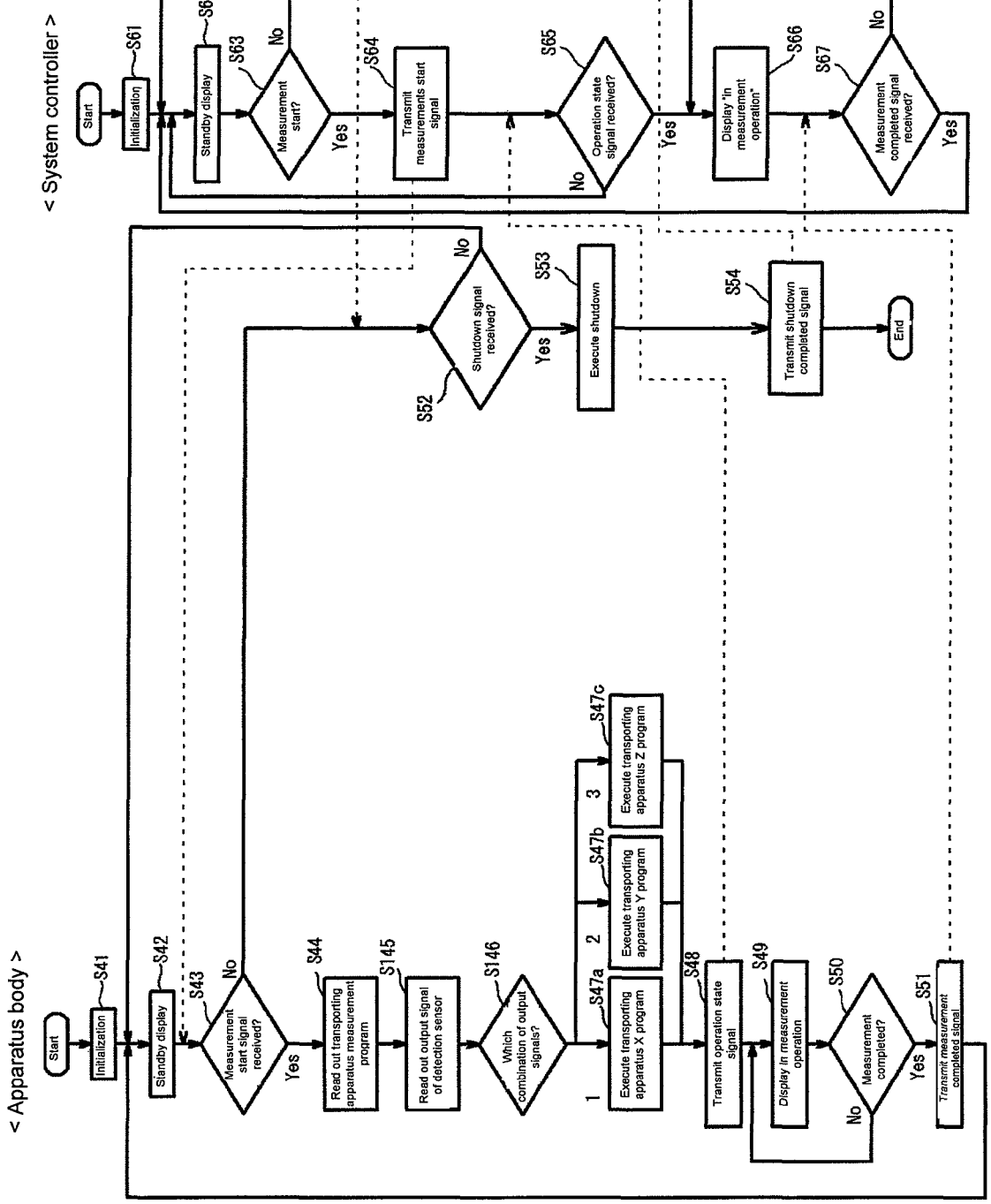
FIG. 24 is a flowchart showing a procedure for the analyzer to perform the transporting apparatus measurement mode according to the second embodiment of the present invention.

FIG. 24 is a flowchart showing a procedure of when the analyzer 10 connected with the transporting apparatus 11 automatically identifies the type of the transporting apparatus, and performs the transporting apparatus measurement mode. The flow chart of FIG. 24 differs from the flowchart of FIG. 19 in steps S145 and S146, and steps S45 and S46, where step S47d is not provided in the flowchart of FIG. 24, but other steps are the same between the flowchart of FIG. 24 and the flowchart of FIG. 19. As shown in FIG. 24, the measurement control unit 16 of the apparatus body 12 reads out the output signals of the detection sensors 43A, 43B in step S145, and determines the combination of the output signals of the detection sensors 43A, 43B (step S146). The measurement control unit 16 executes the transporting apparatus X program when the combination of the output signals of the detection sensors 43A, 43B is (Low, Low) (step S47a), executes the transporting apparatus Y program when the combination of the output signals of the detection sensors 43A, 43B is (Low, High) (step S47b), and executes the transporting apparatus Z program when the combination of the output signals of the detection sensors 43A, 43B is (High, Low) (step S47c). Other processes are similar to the processes in the flowchart of FIG. 13.

As described above, in the second embodiment, the analyzer 10 stores the transporting apparatus program corresponding to a plurality of types (X, Y, Z) of transporting apparatuses 11 in advance in the measurement control unit 16, detects the identification information identifying the connected transporting apparatus 11, selects the transporting apparatus program corresponding to the detected identification information, and executes the relevant program. Thus, the transporting apparatus program does not need to be incorporated for each transporting apparatus 11 connected to the analyzer 10. Therefore, the setting task etc. involved in the connection of the transporting apparatus 11 can be simplified.

The detection of the identification information of the transporting apparatus 11 is performed by the detection sensor 43 by simply connecting the transporting apparatus 11 to the analyzer 10, and thus the setting task etc. involved in the connection of the transporting apparatus 11 can be further simplified.

The type of transporting apparatus for transporting the sample container includes type of hardware of the transporting apparatus, type of software of the transporting apparatus, type of software version of the transporting apparatus, and the like.

The type of hardware includes type indicating a first transporting apparatus configured to transport the rack holding ten sample containers, type indicating a second transporting apparatus configured to transport the rack holding five sample containers, type indicating a third transporting apparatus configured to transport the rack holding one sample container, and the like. The type of hardware also includes model number, model name, and the like of the transporting apparatus.

The type of software includes a first program for controlling the first transporting apparatus, a second program for controlling the second transporting apparatus, and the like.

The type of software version includes a predetermined version (e.g., version 1) of the first program, version 2 or an update program of version 1, and the like.

The analyzer 10 may identify only the type based on the difference in the transporting distance and the feeding pitch of the test tube 32, or identify only the type based on whether or not the transporting apparatus 11 is equipped with the control unit.

In the first embodiment, the set value specifying the transporting apparatus 11 is stored in the memory 21 of the measurement control unit 16, but the present invention is not limited thereto, and may be stored in the hard disc 27d of the system controller 13, so that the system controller 13 transmits the set value to the measurement control unit 16 in the initialization process when activating the analyzer 10 from the next time.

In the second embodiment, the number of detection sensors 43 and the number and configuration of light shielding parts of the light shielding part 42 are determined according to the number of types of the transporting apparatus 11 to be identified. Furthermore, the detection sensor 43 is not limited to an optical sensor, and may be other non-contacting sensor such as proximity sensor or may be a contacting sensor such as micro-switch. The identifying part 42 arranged in the transporting apparatus 11 is not limited to the light shielding plate and may be configured by barcode etc., and the detection means 43 may be appropriately changed according to the mode of the identifying part 42.

In the first embodiment, the operation when the transporting apparatus 11 is not connected to the analyzer 10 is not described, but when the set value "0" identifying the transporting apparatus 11 is input to the input part 29 of the system controller 13 by the user, the set value "0" is transmitted to the measurement control unit 16, the set value "0" is stored in the memory 21 by the control unit 16, and the stored set value "0" is read out, whereby the manual measurement program is executed.

In the second embodiment, the operation when the transporting apparatus 11 is not connected to the analyzer 10 is not described, but if the output signals of the first detection sensor 43A and the second detection sensor 42B of the analyzer 10 is (High, High), the output signals are sent to the control unit 16, and the manual measurement program is executed by the control unit 16.

In the embodiment, description is made on the analyzer for analyzing particles in urine, but the present invention is not limited thereto, and may be applied to a blood analyzer, and other sample processing apparatuses such as a smear preparing apparatus for preparing the smear from the sample.

What is claimed is:

1. A sample processing system for processing a sample contained in a sample container, comprising:
   a transporting apparatus configured to transport a sample container to a predetermined position, the transporting apparatus being selected from plural types of interchangeable transporting apparatuses including a first type and a second type of interchangeable transporting apparatuses, wherein the first type of transporting apparatus is configured to transport a first rack configured to hold a predetermined number of sample containers and the second type of transporting apparatus is configured to transport a second rack configured to hold sample containers of a number different from the predetermined number; and
   a sample processing apparatus configured to process a sample contained in the sample container transported to the predetermined position by the transporting apparatus selected from the plural types of interchangeable transporting apparatuses, the sample processing apparatus comprising:
   a connection part to which each of the plural types of interchangeable transporting apparatuses can be detachably connected;
   an aspirating part configured to aspirate the sample contained in the sample container transported to the predetermined position by the connected transporting apparatus;
   a processing part configured to perform a predetermined process on the sample aspirated by the aspirating part;
   a memory storing a plurality of transport control programs corresponding to the plural types of interchangeable transporting apparatuses respectively, wherein the plurality of transport control programs include a first transport control program and a second transport control program corresponding to the first type and the second type of transporting apparatuses respectively; and
   a controller configured to obtain identification information for identifying a type of the connected transporting apparatus, and control an operation of the connected transporting apparatus by executing one of the plurality of transport control programs stored in the memory corresponding to the type of the connected transporting apparatus based on the obtained identification information.

2. The sample processing system of claim 1, wherein
   the processing part comprises a measuring part configured to measure the sample, or a smear preparing part configured to prepare a smear from the sample.

3. The sample processing system of claim 1, wherein
the transporting apparatus comprises a container detector configured to detect that the sample container is transported to the predetermined position;
the controller controls the aspirating part to aspirate the sample contained in the sample container when the container detector detects that the sample container is transported to the predetermined position, and controls the transporting apparatus so as to transport a next second sample container to the predetermined position after the sample contained in the sample container is aspirated by the aspirating part.

4. The sample processing system of claim 1, comprising an input device, wherein
the controller obtains identification information input by the input device.

5. The sample processing system of claim 4, wherein
the sample processing apparatus comprises
a display; and
the controller displays an input screen on the display, and obtains the identification information input on the input screen by the input device.

6. The sample processing system of claim 5, wherein
the memory stores data which associates the type of the transporting apparatus and an identification number; and
the controller obtains an identification number input on the input screen as the identification information, and controls the operation of the connected transporting apparatus based on the obtained identification number and the data stored in the memory.

7. The sample processing system of claim 1, comprising an identification information detector for detecting the identification information.

8. The sample processing system of claim 7, wherein
the transporting apparatus comprises a detection piece having a form corresponding to the type of the transporting apparatus;
the memory stores data which associates the type of the transporting apparatus and the form of the detection piece;
the identification information detector is configured to detect the form of the detection piece as the identification information; and
the controller controls the operation of the connected transporting apparatus based on the form of the detection piece detected by the identification information detector and the data stored in the memory.

9. The sample processing system of claim 1, wherein
the transporting apparatus comprises a barcode including the identification information; and
the sample processing apparatus comprises a barcode reader configured to read the barcode of the connected transporting apparatus.

10. The sample processing system of claim 1, wherein
a third type of transporting apparatus of the plural types of interchangeable transporting apparatuses comprises a transport controller configured to control an operation of the third type of transporting apparatus and
a fourth type of transporting apparatus of the plural types of interchangeable transporting apparatuses does not comprise a transport controller configured to control an operation of the fourth type of transporting apparatus; and
the plurality of transport control programs include a third transport control program and a fourth transport control program corresponding to the third and fourth types of transporting apparatuses respectively.

11. A sample processing system for processing a sample contained in a sample container, the sample processing system comprising:
a transporting apparatus configured to transport a sample container to a predetermined position, wherein the transporting apparatus is selected from plural types of interchangeable transporting apparatuses including a first type and a second type of interchangeable transporting apparatuses, wherein the first type of transporting apparatus is configured to transport a first rack configured to hold a predetermined number of sample containers and the second type of the transporting apparatus is configured to transport a second rack configured to hold sample containers of a number different from the predetermined number; and
a sample processing apparatus configured to process a sample contained in the sample container transported to the predetermined position by the transporting apparatus selected from the plural types of interchangeable transporting apparatuses,
wherein the sample processing apparatus comprises:
a connection part to which each of the plural types of interchangeable transporting apparatuses can be detachably connected;
an aspirating part configured to aspirate the sample contained in the sample container transported to the predetermined position by the connected transporting apparatus;
a processing part configured to perform a predetermined process on the sample aspirated by the aspirating part;
a first communication part;
a memory storing a plurality of transport control programs corresponding to the plural types of interchangeable transporting apparatuses respectively, wherein the plurality of transport control programs include a first transport control program and a second transport control program corresponding to the first and second types of transporting apparatuses respectively;
a first controller configured to obtain identification information which identifies a type of the connected transporting apparatus, and transmit an operation instructing command to the connected transporting apparatus through the first communication part by executing one of the plurality of the transport control programs stored in the memory corresponding to the type of the connected transporting apparatus, based on the obtained identification information;
and wherein the transporting apparatus further comprises:
a second communication part;
a second controller configured to receive the operation instructing command transmitted from the first communication part through the second communication part and control an operation of the transporting apparatus based on the received operation instructing command.

12. The sample processing system of claim 11, wherein
the second controller transmits transport terminated information indicating that the sample container is transported to the predetermined position to the first communication part through the second communication part; and
the first controller controls the aspirating part so as to aspirate the sample contained in the sample container based on the transport terminated information received through the first communications part from the second communication part.

13. The sample processing system of claim 12, wherein
the first controller transmits aspirate terminated information to the second communication part through the first communication part when a sample aspirating operation by the aspirating part is terminated; and
the second controller controls the operation of the transporting apparatus so as to transport a next sample container to the predetermined position based on the aspirate terminated information received through the second communication part from the first communication part.

14. The sample processing system of claim 12, wherein
the transporting apparatus comprises a container detector configured to detect that the sample container is transported to the predetermined position; and
the second controller transmits the transport terminated information to the first communication part through the second communication part when the container detector detects that the sample container is transported to the predetermined position.

15. A sample processing apparatus for processing a sample contained in a sample container, comprising:
a connection part to which plural types of interchangeable transporting apparatuses including a first type and a second type of interchangeable transporting apparatuses can be detachably connected, wherein the first type of transporting apparatus is configured to transport a first rack configured to hold a predetermined number of sample containers and the second type of transporting apparatus is configured to transport a second rack configured to hold sample containers of a number different from the predetermined number, and each of the plural types of interchangeable transporting apparatuses transports a sample container to a predetermined position;
an aspirating part configured to aspirate a sample contained in the sample container transported to the predetermined position by the connected transporting apparatus;
a processing part configured to perform a predetermined process on the sample aspirated by the aspirating part;
a memory storing a plurality of transport control programs corresponding to the plural types of interchangeable transporting apparatuses respectively, wherein the plurality of transport control programs include a first transport control program and a second transport control program corresponding to the first type and the second type of transporting apparatus respectively; and
a controller configured to obtain identification information which identifies a type of the connected transporting apparatus, and control an operation of the connected transporting apparatus by executing one of the plurality of transport control programs stored in the memory corresponding to the type of the connected transporting apparatus, based on the obtained identification.

16. The sample processing apparatus of claim 15, wherein
the plural types of interchangeable transporting apparatuses include a third of transporting apparatus which can be connected to the connection part;
the plurality of transport control programs stored in the memory include a third transport control program corresponding to the third type of transporting apparatus;
the third type of transport control programs is a communication program for communicating with the third type of transporting apparatus; and
the third type of transporting apparatuses comprises:
a communication part for communicating with the sample processing apparatus;
a transport mechanism configured to transport the sample container; and
a transport controller configured to control an operation of the transport mechanism based on information received through the communication part from the sample processing apparatus.

17. The sample processing apparatus of claim 15, wherein
each of the first type and the second type of transporting apparatus comprises a transport mechanism for transporting the sample container; and
when one of the first and second interchangeable transporting apparatuses is connected to the connection part, the controller controls an operation of the transport mechanism of the connected transporting apparatus by executing one of the first transport control program and the second transport control program corresponding to the type of the connected transporting apparatus, based on the obtained identification information.

\* \* \* \* \*